US007291643B2

(12) United States Patent
McComas et al.

(10) Patent No.: US 7,291,643 B2
(45) Date of Patent: Nov. 6, 2007

(54) CYANOPYRROLE-SULFONAMIDE PROGESTERONE RECEPTOR MODULATORS AND USES THEREOF

(75) Inventors: Casey Cameron McComas, Phoenixville, PA (US); Andrew Fensome, Wayne, PA (US); Edward George Melenski, Collegeville, PA (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 11/494,226

(22) Filed: Jul. 27, 2006

(65) Prior Publication Data

US 2007/0027126 A1 Feb. 1, 2007

Related U.S. Application Data

(60) Provisional application No. 60/704,009, filed on Jul. 29, 2005.

(51) Int. Cl.
*A61K 31/40* (2006.01)
*C07D 207/34* (2006.01)

(52) U.S. Cl. ...................................... 514/427; 548/561

(58) Field of Classification Search ................ 548/561; 514/427

See application file for complete search history.

(56) References Cited

U.S. PATENT DOCUMENTS

| | | | | |
|---|---|---|---|---|
| 4,680,413 | A | 7/1987 | Genda et al. | |
| 4,988,711 | A | 1/1991 | Angerbauer et al. | |
| 5,187,168 | A | 2/1993 | Primeau et al. | |
| 5,223,498 | A | 6/1993 | Gopalan | |
| 5,236,925 | A | 8/1993 | Primeau et al. | |
| 5,310,938 | A | 5/1994 | Brown et al. | |
| 5,455,263 | A | 10/1995 | Doscher et al. | |
| 5,998,459 | A | 12/1999 | Tsuda et al. | |
| 6,013,421 | A | 1/2000 | Nakamura et al. | |
| 6,172,102 | B1 | 1/2001 | Tsuda et al. | |
| 6,664,395 | B2 | 12/2003 | Letavic et al. | |
| 6,696,464 | B2 | 2/2004 | McClure et al. | |
| 2001/0007867 | A1 | 7/2001 | Chen et al. | |
| 2003/0092749 | A1 | 5/2003 | Dombroski et al. | |
| 2005/0239779 | A1* | 10/2005 | Wilk | 514/230.5 |
| 2006/0034786 | A1 | 2/2006 | Michelet et al. | |
| 2006/0089371 | A1 | 4/2006 | Murata et al. | |

FOREIGN PATENT DOCUMENTS

| | | |
|---|---|---|
| EP | 485929 | 5/1992 |
| EP | 487111 | 5/1992 |
| WO | WO-00/66581 | 7/1987 |
| WO | WO-94/17059 | 8/1994 |
| WO | WO-2004/043926 | 5/2004 |
| WO | WO-2004/073594 | 9/2004 |
| WO | WO-2005/105739 | 11/2005 |
| WO | WO-2006/023107 | 3/2006 |
| WO | WO-2006/023109 | 3/2006 |
| ZA | 906550 | 6/1991 |

OTHER PUBLICATIONS

Kiyoshi et al., "Silver Halide Photographic Sensitive Material", Abstract of Japanese Publication No. 2001215668 (Aug. 10, 2001).
Hideaki et al., "Silver Halide Photographic Sensitive Material", Abstract of Japanese Patent Publication No. 2000-122250 (Apr. 28, 2000).
Kiyoshi et al., "Silver Halide Photographic Sensitive Material", Abstract of Japanese Patent Publication No. 2000-122251 (Apr. 28, 2000).
Keiichi, "Image Forming Method", Abstract of Japanese Patent No. 11-352648 (Dec. 24, 1999).
Takemare, "Silver Halide Photographic Sensitive Material and Image Forming Method", Abstract of Japanese Patent No. 10-062895 (Mar. 6, 1998).
Takemare, "Silver Halide Photographic Sensitive Material", Abstract of Japanese Patent No. 07-219176 (Aug. 18, 1995).
Masaaki, "Method for Processing Silver Halide Photographic Sensitive Material", Japanese Patent No. 10-097038 (Apr. 14, 1998).
Collins et al., "Novel Pyrrole-Containing Progesterone Receptor Modulators" Bioorg. & Med. Chem. Lett., 14:2185-2189 (May 3, 2004).
Kleeman et al., "New Substituted Azole and Angiotensin II Receptor Antagonists", English abstract of European Patent No. 485929 (May 20, 1992).

* cited by examiner

*Primary Examiner*—Rebecca Anderson
*Assistant Examiner*—Michael P. Barker
(74) *Attorney, Agent, or Firm*—Arnold S. Milowsky; Howson & Howson LLP

(57) ABSTRACT

Progesterone receptor modulators of formula I, or a pharmaceutically acceptable salt thereof,

I

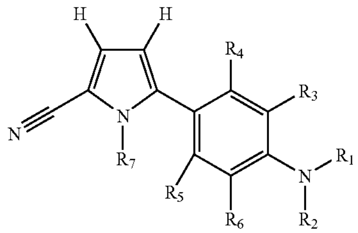

wherein $R_1$, $R_2$, $R_3$, $R_4$, $R_5$, $R_6$ and $R_7$ are as defined herein, are useful for contraception and hormone replacement therapy are described. Also provided are products containing these compounds.

20 Claims, No Drawings

CYANOPYRROLE-SULFONAMIDE PROGESTERONE RECEPTOR MODULATORS AND USES THEREOF

CROSS-REFERENCE TO RELATED APPLICATIONS

This application claims the benefit of the priority of U.S. Provisional Patent Application No. 60/704,009, filed Jul. 29, 2005.

BACKGROUND OF THE INVENTION

Progesterone receptor (PR) agonists and antagonists, also termed PR modulators, have been described for use in contraception and a variety of other indications.

What are needed are novel PR modulators which are useful as contraceptives.

SUMMARY OF THE INVENTION

In one aspect, PR modulators are provided.

In still another aspect, uses of the compounds described herein for contraception, hormone replacement therapy, inducing amenorrhea, synchronizing estrus in livestock, and the treatment and/or prevention of benign and malignant neoplastic disease, uterine myometrial fibroids, endometriosis, benign prostatic hypertrophy, carcinomas and adenocarcinomas of the endometrium, ovary, breast, colon, prostate, pituitary, meningiomal and other hormone-dependent tumors, dysmenorrhea, dysfunctional uterine bleeding, cycle-related symptoms, and symptoms of premenstrual syndrome and premenstrual dysphoric disorder are provided.

In another aspect, pharmaceutical compositions containing the PR modulator are provided.

In a further aspect, pharmaceutical compositions are provided which contain the PR modulator in combination with a progestin or estrogen.

Other aspects and advantages of the present invention are described further in the following detailed description of the preferred embodiments thereof.

DETAILED DESCRIPTION OF THE INVENTION

Compounds useful for contraception, hormone replacement therapy, synchronizing estrus, treating dysmenorrhea, treating dysfunctional uterine bleeding, inducing amenorrhea, treating cycle-related symptoms, or treating symptoms of premenstrual syndrome and premenstrual dysphoric disorder are provided.

A progesterone receptor modulator provided herein is characterized by having the structure of formula I:

I

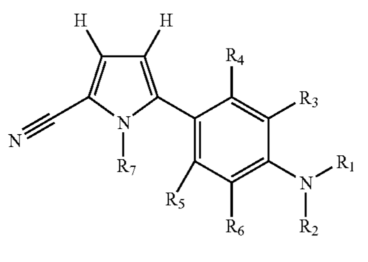

wherein:

$R_1$ is selected from among:

H,

CN, $SO_2$—$C_1$-$C_6$ alkyl, $SO_2$—$C_3$-$C_8$ cycloalkyl, $SO_2$-substituted $C_1$-$C_6$ alkyl, $SO_2$-aryl, $SO_2$-substituted aryl, $SO_2$-heteroaryl, $SO_2$-heterocycle, $SO_2$—$C_3$-$C_6$ alkenyl, $SO_2$—$C_3$-$C_6$ alkynyl, $SO_2$—$C_3$-$C_6$ substituted alkenyl, $SO_2$—$C_3$-$C_6$ substituted alkynyl, C(O)—$C_1$-$C_6$ alkyl, C(O)—$C_3$-$C_8$ cycloalkyl, C(O)-substituted $C_1$-$C_6$ alkyl, C(O)-aryl, C(O)-substituted aryl, C(O)-heteroaryl, C(O)-heterocycle, C(O)—$C_3$-$C_6$ alkenyl, C(O)—$C_3$-$C_6$ alkynyl, C(O)-substituted $C_3$-$C_6$ alkenyl, C(O)-substituted $C_3$-$C_6$ alkynyl, C(O)O—$C_1$-$C_6$ alkyl, C(O)O—$C_3$-$C_8$ cycloalkyl, C(O)O-substituted $C_1$-$C_6$ alkyl, C(O)O-aryl, C(O)O-substituted aryl, C(O)O-heteroaryl, C(O)O-heterocycle, C(O)O—$C_3$-$C_6$ alkenyl, C(O)O—$C_3$-$C_6$ alkynyl, C(O)O—$C_3$-$C_6$ substituted alkenyl, C(O)O—$C_3$-$C_6$ substituted alkynyl, C(O)NH—$C_1$-$C_6$ alkyl, C(O)NH—$C_3$-$C_8$ cycloalkyl, C(O)N-di-$C_3$-$C_8$ cycloalkyl, C(O)N-di-$C_1$-$C_6$ alkyl, C(O)N-di-substituted $C_1$-$C_6$ alkyl, C(O)NH-substituted $C_1$-$C_6$ alkyl, C(O)NH-aryl, C(O)N-di-aryl, C(O)NH-substituted aryl, C(O)N-di-substituted aryl, C(O)NH-heteroaryl, C(O)NH-heterocycle, C(O)N-diheteroaryl, C(O)N-diheterocycle, C(O)NH—$C_3$-$C_6$ alkenyl, C(O)NH—$C_3$-$C_6$ alkynyl, C(O)NH-substituted $C_3$-$C_6$ alkenyl, and C(O)NH-substituted $C_3$-$C_6$ alkynyl; or $R_1$ is a linking group to a second structure of formula I to form a dimer of formula I, said linking group selected from C(O)— or $S(O)_2$—, $R_2$ is selected from among H, $C_1$-$C_6$ alkyl, substituted $C_1$-$C_6$ alkyl, $C_3$-$C_6$ cycloalkyl, $SO_2$-alkyl, and $SO_2$-substituted alkyl;

provided that at least one of $R_1$ or $R_2$ contain a group having an $SO_2$— bound to the N or $R_1$ is a $S(O)_2$— linking group; or $R_1$ and $R_2$ are joined to form $—(C(R_8)_a(R_9)_b)_c—SO_2—(C(R_8)_d(R_9)_e)_f—$;

$R_8$ and $R_9$ are, independently, H, halogen, or $C_1$ to $C_6$ alkyl;

a and b are, independently, 0 to 2, provided that a+b=2;

d and e are, independently, 0 to 2, provided that a+b=2;

c and f are, independently, 0 to 5, provided that one of c or f is greater than 0;

$R_3$, $R_4$, $R_5$ and $R_6$ are independently selected from among H, halogen, CN, $C_1$-$C_6$ alkyl, substituted $C_1$-$C_6$ alkyl, $—(CH_mX_n)_zCH_pX_q$, $C_3$-$C_6$ cycloalkyl, O—$C_1$-$C_6$ alkyl, O—$C_1$-$C_6$ substituted alkyl, O—$(CH_mX_n)_zCH_pX_q$, aryl, heteroaryl, heterocycle, substituted aryl, substituted heteroaryl, and substituted heterocycle;

X is halogen;

m and n are, independently, 0 to 2, provided that m+n=2;

p and q are, independently, 0 to 3, provided that p+q=3;

z is 0 to 10;

$R_7$ is selected from the group consisting of H, $C_1$-$C_6$ alkyl, C(O)O—$C_1$-$C_6$ alkyl, $C_2$ to $C_6$ alkenyl, $C_2$ to $C_6$ alkynyl, substituted $C_1$-$C_6$ alkyl, $C_3$-$C_6$ cycloalkyl, and substituted $C_3$-$C_6$ cycloalkyl.

In one embodiment, the compound has the structure of formula I, wherein:

$R_1$ is H, $SO_2$—$C_1$-$C_6$ (substituted or unsubstituted) alkyl, $SO_2$—$C_3$-$C_6$ cycloalkyl, $SO_2$ (substituted or unsubstituted) aryl, $SO_2$-heteroaryl or CN;

$R_2$ is H or $C_1$-$C_6$ (substituted or unsubstituted) alkyl;

$R_3$, $R_4$, $R_5$ and $R_6$ are independently selected from H, halogen, $C_1$-$C_6$ (substituted or unsubstituted) alkyl, $C_3$-$C_6$ cycloalkyl, and O—$C_1$-$C_6$ (substituted or unsubstituted) alkyl; and $R_7$ is H or $C_1$-$C_6$ alkyl.

In another embodiment, the compound has the structure of formula I, wherein:

$R_1$ is H, $SO_2$—$C_1$-$C_4$ alkyl or CN;

$R_2$ is H;

$R_3$, $R_4$, $R_5$ and $R_6$ are independently selected from H, halogen, $C_1$-$C_6$ (substituted or unsubstituted) alkyl, and O—$C_1$-$C_6$ (substituted or unsubstituted) alkyl; and $R_7$ is H or $C_1$-$C_6$ alkyl.

In another embodiment, the compound has the structure of formula I, wherein:

$R_1$ is $SO_2$—$C_1$-$C_4$ alkyl;

$R_2$ is H;

$R_3$, $R_4$, $R_5$ and $R_6$ are H; and $R_7$ is $C_1$-$C_6$ alkyl.

Thus, in one embodiment, compounds of formula I, wherein $R_1$ or $R_2$ is a $SO_2$-(substituted or unsubstituted) $C_1$-$C_4$ alkyl are provided.

In a further embodiment, N-[4-(5-cyano-1-methyl-1H-pyrrol-2-yl)phenyl]propane-1-sulfonamide; N-[4-(5-cyano-1-methyl-1H-pyrrol-2-yl)phenyl]-N-(methylsulfonyl)methane sulfonamide; N-[4-(5-cyano-1-methyl-1H-pyrrol-2-yl) phenyl]butane-1-sulfonamide; N-[4-(5-cyano-1-methyl-1H-pyrrol-2-yl)phenyl]-2,2,2-trifluoroethanesulfonamide; N-[4-(5-cyano-1-methyl-1H-pyrrol-2-yl)phenyl]-4-isopropylbenzenesulfonamide; N-[4-(5-cyano-1-methyl-1H-pyrrol-2-yl)phenyl]benzenesulfonamide; N-[4-(5-cyano-1-methyl-1H-pyrrol-2-yl)phenyl]-4-methylbenzenesulfonamide; N-[4-(5-cyano-1-methyl-1H-pyrrol-2-yl)phenyl]propane-2-sulfonamide; N-[4-(5-cyano-1-methyl-1H-pyrrol-2-yl)phenyl]ethanesulfonamide; N-[4-(5-cyano-1-methyl-1H-pyrrol-2-yl)phenyl] methanesulfonamide; N-[4-(5-cyano-1-methyl-1H-pyrrol-2-yl)-2-fluorophenyl]methanesulfonamide; N-[4-(5-cyano-1-methyl-1H-pyrrol-2-yl)-2-fluorophenyl] ethanesulfonamide; N-[4-(5-cyano-1-methyl-1H-pyrrol-2-yl)-3-fluorophenyl]ethanesulfonamide; N-[4-(5-cyano-1-methyl-1H-pyrrol-2-yl)-3-fluorophenyl]propane-1-sulfonamide; N-[4-(5-cyano-1-methyl-1H-pyrrol-2-yl)-3-fluorophenyl]butane-1-sulfonamide; N-[4-(5-cyano-1-methyl-1H-pyrrol-2-yl)-3-fluorophenyl]propane-2-sulfonamide; N-[4-(5-cyano-1-methyl-1H-pyrrol-2-yl)-2,5-difluorophenyl]-methane-sulfonamide; N-[4-(5-cyano-1-methyl-1H-pyrrol-2-yl)-2,5-difluorophenyl]ethane-sulfonamide; N-[4-(5-cyano-1-methyl-1H-pyrrol-2-yl)-2,5-difluorophenyl]propane-1-sulfonamide; N-[4-(5-cyano-1-methyl-1H-pyrrol-2-yl)-2,5-difluorophenyl]butane-1-sulfonamide; N-[4-(5-cyano-1-methyl-1H-pyrrol-2-yl)-2,5-difluorophenyl]propane-2-sulfonamide; N-[4-(5-cyano-1-methyl-1H-pyrrol-2-yl)-3-(trifluoromethyl)phenyl] methane-sulfonamide; N-[4-(5-cyano-1-methyl-1H-pyrrol-2-yl)-3-(trifluoromethyl)phenyl]ethane-sulfonamide; N-[4-(5-cyano-1-methyl-1H-pyrrol-2-yl)-3-(trifluoromethyl) phenyl]propane-1-sulfonamide; N-[4-(5-cyano-1-methyl-1H-pyrrol-2-yl)-3-(trifluoromethyl)phenyl]butane-1-sulfonamide; N-[4-(5-cyano-1-methyl-1H-pyrrol-2-yl)-3-(trifluoromethyl)phenyl]propane-2-sulfonamide; N-[4-(5-cyano-1-methyl-1H-pyrrol-2-yl)-2-(trifluoromethoxy) phenyl]methane-sulfonamide; N-[4-(5-cyano-1-methyl-1H-pyrrol-2-yl)-2-(trifluoromethoxy)phenyl]ethane-sulfonamide; N-[4-(5-cyano-1-methyl-1H-pyrrol-2-yl)-2-(trifluoromethoxy)phenyl]propane-1-sulfonamide; N-(4-bromophenyl)ethanesulfonamide; Tert-butyl 2-cyano-5-{4-{(ethylsulfonyl)amino]phenyl}-1H-pyrrole-1-carboxylate; N-[4-(5-cyano-1H-pyrrol-2-yl)phenyl]ethanesulfonamide; N-[4-(5-cyano-1-ethyl-1H-pyrrol-2-yl)phenyl]ethane-sulfonamide; N-[4-(5-cyano-1-propyl-1H-pyrrol-2-yl)phenyl]ethanesulfonamide; N-[4-(1-butyl-5-cyano-1H-pyrrol-2-yl)phenyl]ethanesulfonamide; N-[4-(1-allyl-5-cyano-1H-pyrrol-2-yl)phenyl]ethanesulfonamide; N-[4-(5-cyano-1-prop-2-yn-1-yl-1H-pyrrol-2-yl)phenyl]ethanesulfonamide; N-{4-[5-cyano-1-(3-phenylpropyl)-1H-pyrrol-2-yl] phenyl}ethanesulfonamide; N-[3-cyano-4-(5-cyano-1-methyl-1H-pyrrol-2-yl)phenyl]methanesulfonamide; N-[3-cyano-4-(5-cyano-1-methyl-1H-pyrrol-2-yl)phenyl] ethanesulfonamide; N-[3-cyano-4-(5-cyano-1-methyl-1H-pyrrol-2-yl)phenyl]propane-1-sulfonamide; N-[2-cyano-4-(5-cyano-1-methyl-1H-pyrrol-2-yl)phenyl] methanesulfonamide; N-[4-(5-cyano-1-methyl-1H-pyrrol-2-yl)-3,5-difluorophenyl]-methanesulfonamide; N-[4-(5-cyano-1-methyl-1H-pyrrol-2-yl)-3,5-difluorophenyl] ethane-sulfonamide; N-[4-(5-cyano-1-methyl-1H-pyrrol-2-yl)-3,5-difluorophenyl]propane-1-sulfonamide; N-[4-(5-cyano-1-methyl-1H-pyrrol-2-yl)-3,5-difluorophenyl] butane-1-sulfonamide; N-[4-(5-cyano-1-methyl-1H-pyrrol-2-yl)-3-fluorophenyl]methanesulfonamide, or a pharmaceutically acceptable salt, tautomer, metabolite, or prodrug thereof are provided.

The compounds can contain one or more asymmetric centers and can thus give rise to optical isomers and diastereomers. While shown without respect to stereochemistry, the compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups. In one embodiment, an alkyl group has 1 to about 8 carbon atoms (i.e., $C_1$, $C_2$, $C_3$, $C_4$, $C_5$ $C_6$, $C_7$, or $C_8$). In another embodiment, an alkyl group has 1 to about 6 carbon atoms (i.e., $C_1$, $C_2$, $C_3$, $C_4$, $C_5$ or $C_6$). In a further embodiment, an alkyl group has 1 to about 4 carbon atoms (i.e., $C_1$, $C_2$, $C_3$, or $C_4$).

The term "cycloalkyl" is used herein to refer to cyclic, saturated aliphatic hydrocarbon groups. In one embodiment, a cycloalkyl group has 3 to about 8 carbon atoms (i.e., $C_3$, $C_4$, $C_5$, $C_6$, $C_7$, or $C_8$). In another embodiment, a cycloalkyl group has 3 to about 6 carbon atoms (i.e., $C_3$, $C_4$, $C_5$ or $C_6$).

The term "alkenyl" is used herein to refer to both straight- and branched-chain alkyl groups having one or more carbon-carbon double bonds. In one embodiment, an alkenyl group contains 3 to about 8 carbon atoms (i.e., $C_3$, $C_4$, $C_5$, $C_6$, $C_7$, or $C_8$). In another embodiment, an alkenyl groups has 1 or 2 carbon-carbon double bonds and 3 to about 6 carbon atoms (i.e., $C_3$, $C_4$, $C_5$ or $C_6$).

The term "alkynyl" group is used herein to refer to both straight- and branched-chain alkyl groups having one or more carbon-carbon triple bonds. In one embodiment, an alkynyl group has 3 to about 8 carbon atoms (i.e., $C_3$, $C_4$, $C_5$, $C_6$, $C_7$, or $C_8$). In another embodiment, an alkynyl group contains 1 or 2 carbon-carbon triple bonds and 3 to about 6 carbon atoms (i.e., $C_3$, $C_4$, $C_5$, or $C_6$).

The terms "substituted alkyl", "substituted alkenyl", "substituted alkynyl", and "substituted cycloalkyl" refer to alkyl, alkenyl, alkynyl, and cycloalkyl groups, respectively, having one or more substituents including, without limitation, halogen, CN, OH, $NO_2$, amino, aryl, heterocyclic groups, aryl, alkoxy, aryloxy, alkyloxy, alkylcarbonyl, alkylcarboxy, amino, and arylthio.

The term "aryl" as used herein refers to an aromatic, carbocyclic system, e.g., of about 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio, which groups can be substituted. Desirably, a substituted aryl group is substituted with 1 to about 4 substituents.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring 1 to about 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of about 6 to about 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to about 4 heteroatoms in the backbone of the ring. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, alkylamino, and arylthio. A substituted heterocycle or heteroaryl group may have 1, 2, 3, or 4 substituents.

The term "arylthio" as used herein refers to the S(aryl) group, where the point of attachment is through the sulfur-atom and the aryl group can be substituted as noted above. The term "alkoxy" as used herein refers to the O(alkyl) group, where the point of attachment is through the oxygen-atom and the alkyl group can be substituted as noted above. The term "aryloxy" as used herein refers to the O(aryl) group, where the point of attachment is through the oxygen-atom and the aryl group can be substituted as noted above.

The term "alkylcarbonyl" as used herein refers to the C(O)(alkyl) group, where the point of attachment is through the carbon-atom of the carbonyl moiety and the alkyl group can be substituted as noted above.

The term "alkylcarboxy" as used herein refers to the C(O)O(alkyl) group, where the point of attachment is through the carbon-atom of the carboxy moiety and the alkyl group can be substituted as noted above.

The term "alkylamino" as used herein refers to both secondary and tertiary amines where the point of attachment is through the nitrogen-atom and the alkyl groups can be substituted as noted above. The alkyl groups can be the same or different.

The term "halogen" as used herein refers to Cl, Br, F, or I groups.

The compounds encompass tautomeric forms of the structures provided herein characterized by the bioactivity of the drawn structures. Further, the compounds can be used in the form of salts derived from pharmaceutically or physiologically acceptable bases, alkali metals and alkaline earth metals.

Pharmaceutically acceptable salts may be formed from inorganic bases, desirably alkali metal salts, for example, sodium, lithium, or potassium, and organic bases, such as ammonium, mono-, di-, and trimethylammonium, mono-, di- and triethylammonium, mono-, di- and tripropylammonium (iso and normal), ethyl-dimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmono-ethanolammonium, and the like. Physiologically acceptable alkali salts and alkaline earth metal salts can include, without limitation, sodium, potassium, calcium and magnesium salts in the form of esters, and carbamates.

Other conventional "pro-drug" forms can also be utilized which, when delivered in such form, convert to the active moiety in vivo. Such other compounds can be in the form of esters, carbamates and other conventional "pro-drug" forms, which, when administered in such form, convert to the active moiety in vivo. In one embodiment, the prodrugs are esters. See, e.g., B. Testa and J. Caldwell, “Prodrugs Revisited: The “Ad Hoc” Approach as a Complement to Ligand Design”, Medicinal Research Reviews, 16(3):233-241, ed., John Wiley & Sons (1996).

As described herein, the compounds of formula I and/or salts, prodrugs or tautomers thereof, are delivered in regimens for contraception, therapeutic or prophylactic purposes, as described herein.

The compounds discussed herein also encompass “metabolites” which are unique products formed by processing the compounds by the cell or patient. Desirably, metabolites are formed in vivo.

The compounds are readily prepared by one of skill in the art according to the following schemes from commercially available starting materials or starting materials which can be prepared using literature procedures. These schemes show the preparation of representative compounds. Variations on these methods, or other methods known in the art, can be readily utilized by one of skill in the art given the information provided herein.

Scheme 1

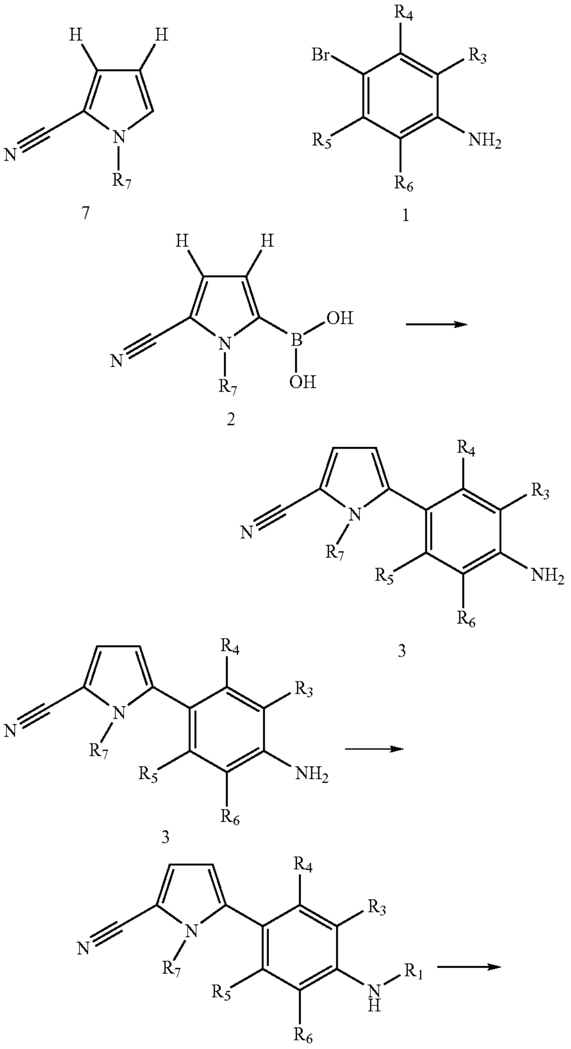

7

1

2

3

3

4

-continued

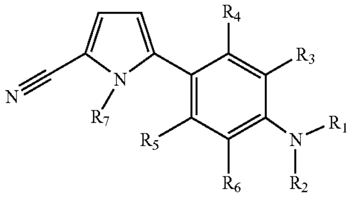

5

According to scheme 1, an appropriately substituted bromoaniline (1) is converted into compound 3 under the action of a palladium catalyst and a suitable coupling partner such as a boronic acid or tin derivative. The aniline may also be a chloro, iodo, or sulfonate derivative. The coupling partner may be formed in situ from the pyrrole (7) and lithium diisopropylamide and a trialkyl borate or may be the preformed boronic acid (2) as described in co-owned US Patent Application Publication No. US-2005-0272702-A1, which is hereby incorporated by reference. The source of palladium is normally tetrakis(triphenylphosphine) palladium (0) or another suitable source such as palladium dibenzylidene acetone in the presence of tributylphosphine (Fu, G. C. et al. Journal of the American Chemical Society, 2000, 122, 4020). Alternate catalyst systems are described in Hartwig, et al. Journal of Organic Chemistry, 2002, 67, 5553. A base is also required in the reaction; the normal choices are sodium or potassium carbonate, cesium fluoride, potassium fluoride, or potassium phosphate. The choice of solvents includes tetrahydrofuran (THF), dimethoxyethane (DME), dioxane, ethanol, water, and toluene. Depending on the reactivity of the coupling partners and reagents, the reaction may be conducted up to the boiling point of the solvent, or may indeed be accelerated under microwave irradiation, if necessary.

Compounds 4, where $R_1$ includes an amide, are readily accessible from compounds 3 by reaction with a wide variety of electrophilic reagents including acid chlorides and carboxylic acids combined with an activating reagent such as dicyclohexyl-carbodiimide (DCC), N-(3-Dimethylaminopropyl)-N'-ethylcarbodiimide hydrochloride (EDC), benzotriazol-1-yl-oxytripyrrolidinophosphonium hexafluorophosphate (the PyBOP® reagent); or for further examples see, e.g., R. C. Larock, “Comprehensive Organic Transformations”, Second Edition, John Wiley & Sons (1999). Compounds 4, where $R_1$ includes a carbamate, are readily accessible from 3 by reaction with a wide variety of electrophilic reagents including chloroformates or activated carbonates. Compounds 4, where $R_1$ includes a sulfonamide, are readily accessible from compounds 3 by reaction with a wide variety of electrophilic reagents including sulfonyl chlorides or sulfonic acids combined with an activating reagent. Compounds 4, where $R_1$ includes a cyanamide, are readily accessible from compounds 3 by reaction with electrophilic reagents such as cyanogen bromide. Compounds 4, where $R_1$ includes a urea, are readily accessible from compounds 3 by reaction with a wide variety of electrophilic reagents including phosgene (followed by reaction with an amine), carbamoyl chlorides, and isocyanates. These reactions are conducted in a suitable solvent including methylene chloride, THF, dimethylformamide (DMF), or pyridine in the presence of an amine base such as pyridine, triethylamine, or diisopropylethyl amine. Metal salts including sodium carbonate, cesium carbonate, potassium carbonate, are also suitable bases for the reaction. The aniline 3 may also be pretreated with a strong base, including alkyl lithium bases, potassium tertiary butoxide, sodium hexamethyldisilazide and similar bases in an aprotic solvent such as ether or THF and then reacted with the electrophilic reagent. Alternatively, the aniline 3 may be directly dissolved in an acid chloride, sulfonyl chloride, or chloroformate in the absence of solvent or base to generate compounds 4.

Compounds 5 are readily accessible from compounds 4 by reaction with a wide variety of electrophilic reagents such as acid chlorides, sulfonyl chlorides, chloroformates, cyanogen bromide, isocyanates, and alkylating agents. Alkylating agents are commonly comprised of an alkane possessing a suitable leaving group such as a bromide, iodide, chloride, or sulfonate. Common examples of alkylating agents are methyl iodide, benzyl bromide, propyl bromide, allyl chloride, and propargyl bromide. The corresponding carboxylic acid or sulfonic acid derivative and a suitable activating reagent can also be reacted with compounds 4 to give compounds 5. These reactions are conducted in a suitable solvent including methylene chloride, THF, DMF, or pyridine in the presence of an amine base such as pyridine, triethylamine, or diisopropylethyl amine. Metal salts including sodium carbonate, cesium carbonate, or potassium carbonate are also suitable bases for the reaction. The aniline derivative 4 may also be pretreated with a strong base, including an alkyl lithium base, potassium tertiary butoxide, sodium hexamethyldisilazide and similar bases in an aprotic solvent such as ether or THF and then reacted with the electrophilic reagent. Alternatively the aniline derivative 4 may be directly dissolved in an acid chloride, sulfonyl chloride, or chloroformate in the absence of solvent or base to generate compounds 5.

Scheme 2

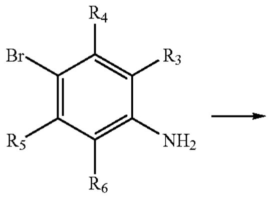

1

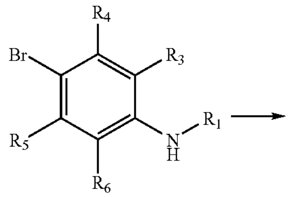

8

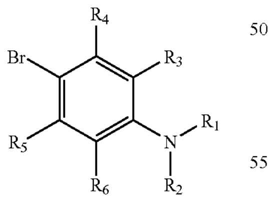

9

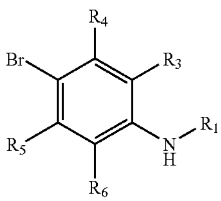

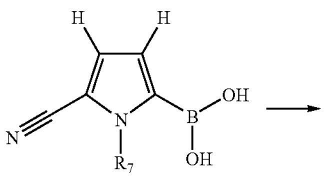

2

-continued

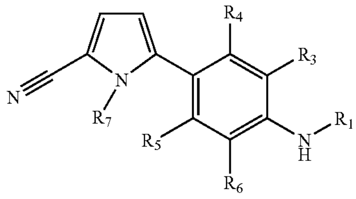

4

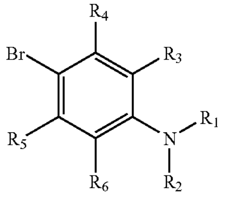

9

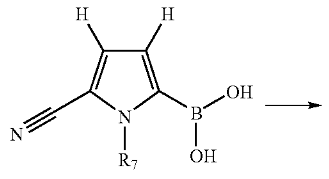

2

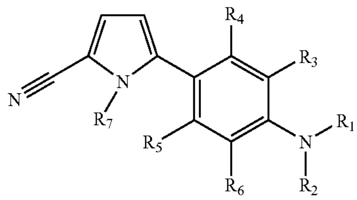

5

An alternative method for the production of compounds 4 and 5 is shown in Scheme 2. Compounds 8, where $R_1$ includes an amide, are readily accessible from aniline 1 by reaction with a wide variety of electrophilic reagents including acid chlorides and carboxylic acids combined with an activating reagent. Compounds 8, where $R_1$ includes a carbamate, are readily accessible from aniline 1 by reaction with a wide variety of electrophilic reagents including chloroformates or activated carbonates. Compounds 8, where $R_1$ includes a sulfonamide, are readily accessible from aniline 1 by reaction with a wide variety of electrophilic reagents including sulfonyl chlorides or sulfonic acids combined with an activating reagent such as $PCl_5$, $POCl_3$, DCC, EDC, the PyBOP® reagent, or for further examples see, e.g., R. C. Larock, "Comprehensive Organic Transformations", Second Edition, John Wiley & Sons (1999). Compounds 8, where $R_1$ includes a cyanamide, are readily accessible from aniline 1 by reaction electrophilic reagents such as cyanogen bromide. Compounds 8, where $R_1$ includes a urea, are readily accessible from aniline 1 by reaction with a wide variety of electrophilic reagents including phosgene, triphosgene, diphosgene, carbonyl diimidazole, carbamoyl chlorides, and isocyanates. These reactions are conducted in a suitable solvent including methylene chloride, THF, DMF, or pyridine in the presence of an amine base such as pyridine, triethylamine, or diisopropylethyl amine. Metal salts including sodium carbonate, cesium carbonate, or potassium carbonate are also suitable bases for the reaction. The aniline 1 may also be pretreated with a strong base, including alkyl lithium bases, potassium tertiary butoxide, sodium hexamethyldisilazide and similar bases in an aprotic solvent such as ether or THF and then reacted with the electrophilic reagent. Alternatively the aniline 1 may be directly dissolved in an acid chlorides, sulfonyl chlorides, or chloroformate in the absence of solvent or base to generate compounds 8.

Bromoaniline compounds 9 are readily accessible from substituted bromoaniline compounds 8 by reaction with a wide variety of electrophilic reagents such as acid chlorides, sulfonyl chlorides, chloroformates, cyanogen bromide, isocyanates, and alkylating agents. Alkylating agents are commonly comprised of an alkane possessing a suitable leaving group such as a bromide, iodide, chloride, or sulfonate. Common examples of alkylating agents are methyl iodide, benzyl bromide, propyl bromide, allyl chloride, and propargyl bromide. The corresponding carboxylic acid or sulfonic acid derivative and a suitable activating reagent can also be reacted with compounds 8 to give compounds 9. These reactions are conducted in a suitable solvent including methylene chloride, THF, DMF, or pyridine in the presence of an amine base such as pyridine, triethylamine, or diisopropylethyl amine. Metal salts including sodium carbonate, cesium carbonate, or potassium carbonate are also suitable bases for the reaction. The aniline derivative 8 may also be pretreated with a strong base, including alkyl lithium bases, potassium tertiary butoxide, sodium hexamethyldisilazide and similar bases in an aprotic solvent such as ether or THF and then reacted with the electrophilic reagent. Alternatively the aniline derivative 8 may be directly dissolved in an acid chloride, sulfonyl chloride, or chloroformate in the absence of solvent or base to generate compounds 9.

The substituted bromoaniline 8 or bromoaniline 9 is converted into compound 4 or compound 5 respectively, under the action of a palladium catalyst and a suitable coupling partner such as a boronic acid or tin derivative. The aniline may also be a chloro, iodo, or sulfonate derivative. The coupling partner may be formed in situ from the pyrrole (7) (see, scheme 1) and lithium diisopropylamide and a trialkyl borate or may be the pre-formed boronic acid (2). The source of palladium is normally tetrakis(triphenylphosphine) palladium (0) or another suitable source such as palladium dibenzylidene acetone in the presence of tributylphosphine (Fu, G. C. et al. Journal of the American Chemical Society, 2000, 122, 4020, for alternate catalyst systems see also Hartwig, J. F. et al. *Journal of Organic Chemistry,* 2002, 67, 5553). A base is also required in the reaction and the normal choices are sodium or potassium carbonate, cesium fluoride, potassium fluoride, or potassium phosphate. The choice of solvents includes THF, dimethoxyethane, dioxane, ethanol, water, and toluene. Depending on the reactivity of the coupling partners and reagents, the reaction may be conducted up to the boiling point of the solvents, or may indeed be accelerated under microwave irradiation, if necessary.

Also described are pharmaceutical compositions containing one or more compounds discussed herein and a pharmaceutically acceptable carrier or excipient. These compounds and compositions can be used in methods of treatment which include administering to a mammal a pharmaceutically effective amount of one or more compounds as described above as modulators of the progesterone receptor.

The compounds can be utilized in methods of contraception, hormone replacement therapy, and the treatment and/or prevention of benign and malignant neoplastic disease, uterine myometrial fibroids, endometriosis, benign prostatic hypertrophy; carcinomas and adenocarcinomas of the endometrium, ovary, breast, colon, prostate, pituitary, meningioma and other hormone-dependent tumors, dysmenorrhea, dysfunctional uterine bleeding, cycle-related symptoms, and symptoms of premenstrual syndrome and premenstrual dysphoric disorder; and for inducing amenorrhea. Additional uses of the present progesterone receptor modulators include the synchronization of estrus in livestock.

The term “cycle-related symptoms” refers to psychological and physical symptoms associated with a woman’s menstrual cycle arising in the luteal phase of the menstrual cycle. It has been reported that most women report experiencing cycle-related symptoms. The symptoms generally disappear after the onset of menstruation, and the patient is free from symptoms during the rest of the follicular phase. The cyclical nature of the symptom variations is characteristic of cycle-related symptoms.

Cycle-related symptoms occur in about 95% of women who experience some physical or mood changes with their menstrual cycles. Only about one-third of those women experiences moderate to severe cycle-related symptoms. Women vary in the number, type, severity, and pattern of symptoms before menstruation. One thing common to all the types of cyclic-related symptoms is the decrease or elimination of the symptoms in the two weeks after menstruation up to ovulation.

The term “cycle-related symptoms” refers to psychological symptoms (for example, mood change, irritability, anxiety, lack of concentration, or decrease in sexual desire) and physical symptoms (for example, dysmenorrhea, breast tenderness, bloating, fatigue, or food cravings) associated with a woman’s menstrual cycle. Cycle-related symptoms occur after ovulation but before menses and usually terminate at the start of the menstrual period or shortly thereafter. Cycle-related symptoms include, but are not limited to, dysmenorrhea and moderate to severe cycle-related symptoms.

Suitably, the PR modulators are formulated for delivery by any suitable route including, e.g., transdermal, mucosal (intranasal, buccal, vaginal), oral, parenteral, etc, by any suitable delivery device including, e.g., transdermal patches, topical creams or gels, a vaginal ring, among others.

When the compounds are employed for the above utilities, they may be combined with one or more pharmaceutically acceptable carriers or excipients, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. In one embodiment, satisfactory results are obtained when the compounds are administered at a daily dosage of from about 0.5 to about 500 mg/kg of animal body weight, desirably given in divided doses one to four times a day, or in a sustained release form. In another embodiment, for most large mammals, the total daily dosage is from about 1 to 100 mg. In another embodiment, the total daily dosage is from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, butylated hydroxytoluene (BHT) and butylated hydroxyanisole (BHA).

The pharmaceutical compositions from the standpoint of ease of preparation and administration are solid compositions, particularly tablets and hard-filled or liquid-filled capsules. Oral administration of the compounds is desirable.

The compounds may also be administered parenterally or intraperitoneally. Solutions or suspensions of the compounds as a free base or pharmacologically acceptable salt can be prepared in water suitably mixed with a surfactant such as hydroxypropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The compounds may also be administered via a vaginal ring. Suitably, use of the vaginal ring is timed to the 28 day cycle. In one embodiment, the ring is inserted into the vagina, and it remains in place for 3 weeks. During the fourth week, the vaginal ring is removed and menses occurs. The following week a new ring is inserted to be worn another 3 weeks until it is time for the next period. In another embodiment, the vaginal ring is inserted weekly, and is replaced for three consecutive weeks. Then, following one week without the ring, a new ring is inserted to begin a new regimen. In yet another embodiment, the vaginal ring is inserted for longer or shorter periods of time.

For use in the vaginal ring, a PR modulator compound is formulated in a manner similar to that described for contraceptive compounds previously described for delivery via a vaginal ring. See, e.g., U.S. Pat. Nos. 5,972,372; 6,126,958 and 6,125,850.

In still another aspect, the PR modulator compound(s) are delivered via a transdermal patch. Suitably, use of the patch is timed to the 28 day cycle. In one embodiment, the patch is applied via a suitable adhesive on the skin, where it remains in place for 1 week and is replaced weekly for a total period of three weeks. During the fourth week, no patch is applied and menses occurs. The following week a new patch is applied to be worn to begin a new regimen. In yet another embodiment, the patch remains in place for longer, or shorter periods of time.

In one embodiment, the PR modulator(s) are used in cyclic regimens involving administration of the PR modulator alone. In another embodiment, the cyclic regimen involves administration of a PR modulator in combination with an estrogen or progestin, or both. Particularly desirable progestins can be selected from among those described in U.S. Pat. Nos. 6,355,648; 6,521,657; 6,436,929; 6,540,710; and 6,562,857 and US Patent Application Publication No. 2004-0006060-A1. Still other progestins are known in the art and can be readily selected. In one embodiment, combination regimens with the PR agonist (i.e., progestin) tanaproget 5-(4,4-dimethyl-2-thioxo-1,4-dihydro-2H-3,1-benzoxazin-6-yl)-1-methyl-1H-pyrrole-2-carbonitrile are provided.

Further included are administration regimens carried out over 28 consecutive days. These regimens may be continuous or may involve a terminal portion of the cycle, e.g., 0 to 7 days, containing administration of no progestins, estrogens or anti-progestins. See, e.g., the regimens described in US Patent Application Publication No. US-2006-0009509-A1, which is hereby incorporated by reference.

The regimens described herein may be utilized for contraception, or for any of the other indications described herein. Where administration is for contraception, the compositions may be formulated in oral dosage units.

When utilized for contraception, the PR modulators may be administered to a female of child bearing age, alone or in combination with an estrogen. For the first 14 to 24 days of the cycle, a progestational agent is administered, desirably at a dosage range equal in progestational activity to about 35 μg to about 150 μg levonorgestrel per day, and more desirably equal in activity to about 35 μg to about 100 μg levonorgestrel per day. A PR modulator may then be administered alone or in combination with an estrogen for a period of 1 to 11 days to begin on any cycle day between day 14 and 24. The PR modulator in these combinations may be administered at a dose of from about 2 μg to about 50 μg per day and the estrogen may be administered at a dose of from about 10 μg to about 35 μg per day. In an oral administration, a package or kit containing 28 tablets will include a placebo tablet on those days when the PR modulator or progestin or estrogen is not administered.

Progestational agents useful herein include, but are not limited to, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, or (17-deacetyl)norgestimate. Among the desirable progestins for use in the combinations are levonorgestrel, gestodene and trimegestone.

Examples of orally administered regimens over a 28 day cycle include administration of a progestational agent solely for the first 21 days at a daily dose equal in progestational activity to from about 35 to about 100 μg of levonorgestrel. A PR modulator compound can then be administered at a daily dose of from about 1 to 200 mg from day 22 to day 24, followed by no administration or administration of a placebo for days 25 to 28. It is most desirable that the daily dosages of each relevant active ingredient be incorporated into a combined, single daily dosage unit, totaling 28 daily units per 28-day cycle.

In another regimen, a progestational agent may be co-administered for the first 21 days at a daily dose equal in progestational activity to from about 35 to about 150 μg levonorgestrel, desirably equal in activity to from about 35 to about 100 μg levonorgestrel, with an estrogen, such as ethinyl estradiol, at a daily dose range of from about 10 to about 35 μg. This may be followed as described above with a PR modulator administered at a daily dose of from about 1 to 250 mg from day 22 to day 24, followed by no administration or administration of a placebo for days 25 to 28.

Still another regimen will include co-administration from days 1 to 21 of a progestational agent, e.g., levonorgestrel, being administered at a daily dose equal in progestational activity to from about 35 to about 100 μg levonorgestrel, and an estrogen, such as ethinyl estradiol, at a daily dose range of from about 10 to about 35 μg. This will be followed on days 22 to 24 by co-administration of a PR modulator (1 to 250 mg/day) and an estrogen, such as ethinyl estradiol, at a daily dose of from about 10 to about 35 μg. From day 25 to day 28, this regimen may be followed by no administration or administration of a placebo.

The compounds and compositions can be included in kits or packages of pharmaceutical formulations designed for use in the regimens described herein. These kits are desirably designed for daily oral administration over a 28-day cycle, desirably for one oral administration per day, and organized so as to indicate a single oral formulation or combination of oral formulations to be taken on each day of the 28-day cycle. Desirably, each kit will include oral tablets to be taken on each the days specified, desirably one oral tablet will contain each of the combined daily dosages indicated.

According to the regimens described above, one 28-day kit may contain (a) an initial phase of from 14 to 21 daily dosage units of a progestational agent equal in progestational activity to about 35 to about 150 μg levonorgestrel, desirably equal in progestational activity to about 35 to about 100 μg levonorgestrel; (b) a second phase of from 1 to 11 daily dosage units of a PR modulator compound, each daily dosage unit containing the PR modulator compound at a daily dosage of from about 1 to 250 mg; and (c) optionally, a third phase of an orally and pharmaceutically acceptable placebo for the remaining days of the cycle in which no PR modulator (i.e., antiprogestin or progestin) or estrogen is administered.

In one embodiment of this kit, the initial phase involves 21 daily dosage units as described in the preceding passage, a second phase of 3 daily dosage units for days 22 to 24 of a PR modulator compound and an optional third phase of 4 daily units of an orally and pharmaceutically acceptable placebo for each of days 25 to 28.

In another embodiment, a 28-day cycle packaged regimen or kit contains, a first phase of from 18 to 21 daily dosage units, and more desirably, 21 days, as described in the preceding passages, and, further including, as an estrogen, ethinyl estradiol at a daily dose range of from about 10 to about 35 μg; a second phase of from 1 to 7 daily dosage units, and desirably, 4 daily dosage units, as described above, and an optional placebo for each of the remaining 0-9 days, or about 4 days, in the 28-day cycle in which no progestational agent, estrogen or antiprogestin is administered.

A further 28-day packaged regimen or kit includes (a) a first phase of from 18 to 21 daily dosage units, each containing a progestational agent at a daily dose equal in progestational activity to about 35 to about 150 μg levonorgestrel, desirably equal in activity to from about 35 to about 100 μg levonorgestrel, and ethinyl estradiol at a daily dose range of from about 10 to about 35 μg; (b) a second phase of from 1 to 7 daily dose units, each daily dose unit containing a PR modulator at a concentration of from 1 to 250 mg and ethinyl estradiol at a concentration of from about 10 to about 35 μg; and (c) optionally, an orally and pharmaceutically acceptable placebo for each of the remaining 0-9 days in the 28-day cycle in which no progestational agent, estrogen or antiprogestin is administered.

In one embodiment, the package or kit just described includes a first phase of 21 daily dosage units; a second phase of 3 daily dosage units for days 22 to 24, each daily dose unit containing an PR modulator at a concentration of from 2 to 200 mg and ethinyl estradiol at a concentration of from about 10 to about 35 μg; and optionally, a third phase of 4 daily units of an orally and pharmaceutically acceptable placebo for each of days 25 to 28.

In each of the regimens and kits just described, it is desirable that the daily dosage of each pharmaceutically active component of the regimen remain fixed in each particular phase in which it is administered. It is also understood that the daily dose units described are to be administered in the order described, with the first phase followed in order by the second and third phases. To help facilitate compliance with each regimen, it is also desirable that the kits contain the placebo described for the final days of the cycle. It is further desirable that each package or kit comprise a pharmaceutically acceptable package having indicators for each day of the 28-day cycle, such as a labeled blister package or dial dispenser packages known in the art.

As used herein, the terms anti-progestational agents, anti-progestins and progesterone receptor antagonists are understood to be synonymous. Similarly, progestins, progestational agents and progesterone receptor agonists are understood to refer to compounds of the same activity.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

The compounds and compositions can further be provided in kits and delivery devices for a variety of other therapeutic uses as described herein including, e.g., hormone replacement therapy, the treatment and/or prevention of benign and malignant neoplastic disease. Such kits contain components in addition to the compounds, including, e.g., instructions for delivery of the compounds, diluents, vials, syringes, packaging, among other items.

Such kits may optionally be adapted for the selected application, e.g., hormone replacement therapy, treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors, dysmenorrhea, dysfunctional uterine bleeding, cycle-related symptoms, and symptoms of premenstrual syndrome and premenstrual dysphoric disorder; for inducing amenorrhea; or the synchronization of the estrus in livestock.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

N-[4-(5-cyano-1-methyl-1H-pyrrol-2-yl)phenyl] propane-1-sulfonamide

The general procedure for sulfonylation of 5-(4-aminophenyl)-1-methyl-1H-pyrrole-2-carbonitrile is as follows.

5-(4-Aminophenyl)-1-methyl-1H-pyrrole-2-carbonitrile (98 mg, 0.5 mmol) was dissolved in dichloromethane (2 mL) and triethylamine (87 μL, 0.6 mmol) was added. Propane sulfonyl chloride (62 μL, 0.55 mmol) was added and the mixture was stirred 16 hours. The mixture was diluted with 50% ether in ethyl acetate and washed with water, saturated $NaHCO_3$, 2N HCl, brine, dried over $MgSO_4$, and concentrated. Flash chromatography (0%-100% ethyl acetate in hexane) afforded N-[4-(5-cyano-1-methyl-1H-pyrrol-2-yl)phenyl]propane-1-sulfonamide (0.039 g).

HPLC purity 97.8% at 210-370 nm, 8.8 min.; 97.7% at 284 nm, 8.8 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{15}H_{17}N_3O_2S+H^+$, 304.11142; found (ESI-FTMS, $[M+H]^+$), 304.11165.

Example 2

N-[4-(5-cyano-1-methyl-1H-pyrrol-2-yl)phenyl]-N-(methylsulfonyl)methane sulfonamide The title compound was prepared according to general procedure for sulfonylation of 5-(4-aminophenyl)-1-methyl-1H-pyrrole-2-carbonitrile using methane sulfonyl chloride (43 μL, 0.55 mmol) to provide N-[4-(5-cyano-1-methyl-1H-pyrrol-2-yl)phenyl]-N-(methylsulfonyl)methanesulfonamide (0.021 g).

HPLC purity 95.3% at 210-370 nm, 8.0 min.; 95.3% at 290 nm, 8.0 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{14}H_{15}N_3O_4S_2+H^+$, 354.05767; found (ESI-FTMS, $[M+H]^+$), 354.05748.

Example 3

N-[4-(5-cyano-1-methyl-1H-pyrrol-2-yl)phenyl] butane-1-sulfonamide

The title compound was prepared according to general procedure for sulfonylation of 5-(4-aminophenyl)-1-methyl-1H-pyrrole-2-carbonitrile using butane sulfonyl chloride (72 μL, 0.55 mmol) to provide N-[4-(5-cyano-1-methyl-1H-pyrrol-2-yl)phenyl]butane-1-sulfonamide (0.026 g).

HPLC purity 98.9% at 210-370 nm, 9.3 min.; 98.9% at 284 nm, 9.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{16}H_{19}N_3O_2S+H^+$, 318.12707; found (ESI-FTMS, $[M+H]^+$), 318.12729.

Example 4

N-[4-(5-cyano-1-methyl-1H-pyrrol-2-yl)phenyl]-2,2,2-trifluoroethanesulfonamide

The title compound was prepared according to general procedure for sulfonylation of 5-(4-aminophenyl)-1-methyl-1H-pyrrole-2-carbonitrile using 2,2,2-trifluoro-ethanesulfonyl chloride (55 μL, 0.55 mmol) to provide N-[4-(5-cyano-1-methyl-1H-pyrrol-2-yl)phenyl]-2,2,2-trifluoroethanesulfonamide (0.014 g).

HPLC purity 100% at 210-370 nm, 9.0 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min.

Example 5

N-[4-(5-cyano-1-methyl-1H-pyrrol-2-yl)phenyl]-4-isopropylbenzenesulfonamide

The title compound was prepared according to general procedure for sulfonylation of 5-(4-aminophenyl)-1-methyl-1H-pyrrole-2-carbonitrile using 4-isopropyl-benzenesulfonyl chloride (120 mg, 0.55 mmol) to provide N-[4-(5-cyano-1-methyl-1H-pyrrol-2-yl)phenyl]4-isopropylbenzenesulfonamide (0.049 g).

HPLC purity 97.2% at 210-370 nm, 10.3 min.; 97.2% at 286 nm, 10.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{21}H_{21}N_3O_2S+H^+$, 380.14272; found (ESI-FTMS, $[M+H]^+$), 380.14319.

Example 6

N-[4-(5-cyano-1-methyl-1H-pyrrol-2-yl)phenyl] benzenesulfonamide

The title compound was prepared according to general procedure for sulfonylation of 5-(4-aminophenyl)-1-methyl-1H-pyrrole-2-carbonitrile using benzenesulfonyl chloride (70 μL, 0.55 mmol) to provide N-[4-(5-cyano-1-methyl-1H-pyrrol-2-yl)phenyl]benzene sulfonamide (0.046 g).

HPLC purity 93.0% at 210-370 nm, 9.3 min.; 94.8% at 286 nm, 9.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{18}H_{15}N_3O_2S+H^+$, 338.09577; found (ESI-FTMS, $[M+H]^+$), 338.09611.

Example 7

N-[4-(5-cyano-1-methyl-1H-pyrrol-2-yl)phenyl]-4-methylbenzenesulfonamide

The title compound was prepared according to general procedure for sulfonylation of 5-(4-aminophenyl)-1-methyl-1H-pyrrole-2-carbonitrile using p-toluenesulfonyl chloride (105 mg, 0.55 mmol) to provide N-[4-(5-cyano-1-methyl-1H-pyrrol-2-yl)phenyl]-4-methyl benzenesulfonamide (0.036 g).

HPLC purity 98.3% at 210-370 nm, 9.7 min.; 97.8% at 286 nm, 9.7 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{19}H_{17}N_3O_2S+H^+$, 352.11142; found (ESI-FTMS, $[M+H]^{1+}$), 352.11183.

Example 8

N-[4-(5-cyano-1-methyl-1H-pyrrol-2-yl)phenyl] propane-2-sulfonamide 5-(4-Aminophenyl)-1-methyl-1H-pyrrole-2-carbonitrile (0.27 g, 1.37 mmol) was dissolved in isopropyl sulfonyl chloride (0.50 mL, 2.8 mmol) and heated to 70° C. for 6 hours. The mixture was cooled and diluted with water and extracted with ethyl acetate. The organics were combined, washed with water, brine, dried over $MgSO_4$, and concentrated. Flash chromatography (0%-100% ethyl acetate in hexane) afforded N-[4-(5-cyano-1-methyl-1H-pyrrol-2-yl)phenyl]propane-2-sulfonamide (0.009 g).

HPLC purity 94.7% at 210-370 nm, 8.8 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{15}H_{17}N_3O_2S$+H+, 304.1114; found (ESI, $[M+H]^+$), 304.1132.

Example 9

N-[4-(5-cyano-1-methyl-1H-pyrrol-2-yl)phenyl]ethanesulfonamide 5-(4-Aminophenyl)-1-methyl-1H-pyrrole-2-carbonitrile (1.3 g, 6 mmol) was dissolved in pyridine (10 mL), ethane sulfonyl chloride (0.54 mL, 5.7 mmol) was added, the mixture was stirred for 4 hours, and then water was added. The mixture was diluted with ethyl acetate and washed with water, saturated $CuSO_4$, 2N HCl, brine, dried over $MgSO_4$, and concentrated. Flash chromatography (5%-50% ethyl acetate in hexane) afforded N-[4-(5-cyano-1-methyl-1H-pyrrol-2-yl)phenyl]ethanesulfonamide (1.33 g).

HPLC purity 100% at 210-370 nm, 8.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{14}H_{15}N_3O_2S+H^+$, 290.09577; found (ESI, $[M+H]^+$), 290.0958.

Example 10

N-[4-(5-cyano-1-methyl-1H-pyrrol-2-yl)phenyl]methanesulfonamide 5-(4-Aminophenyl)-1-methyl-1H-pyrrole-2-carbonitrile (0.5 g, 2.3 mmol) was dissolved in pyridine (5 mL), methane sulfonyl chloride (0.16 mL, 2.1 mmol) was added, the mixture was stirred for 4 hours, and then water was added. The mixture diluted with ethyl acetate and the mixture was washed with water, saturated $CuSO_4$, 2N HCl, brine, dried over $MgSO_4$, and concentrated. Flash chromatography (5%-50% ethyl acetate in hexane) afforded N-[4-(5-cyano-1-methyl-1H-pyrrol-2-yl)phenyl]methanesulfonamide (0.382 g).

MS (ES) m/z 276.1; HPLC purity 100% at 210-370 nm, 7.9 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min.

Example 11

N-[4-(5-cyano-1-methyl-1H-pyrrol-2-yl)-2-fluorophenyl]methanesulfonamide 5-(4-amino-3-fluorophenyl)-1-methyl-1H-pyrrole-2-carbonitrile (0.15 g, 0.70 mmol) was dissolved in pyridine (1.5 mL), methane sulfonyl chloride (0.05 mL, 0.63 mmol) was added, the mixture was stirred for 4 hours, and then water was added. The mixture diluted with ethyl acetate and the mixture was washed with water, saturated $CuSO_4$, 2N HCl, brine, dried over $MgSO_4$, and concentrated. Flash chromatography (5%-50% ethyl acetate in hexane) afforded N-[4-(5-cyano-1-methyl-1H-pyrrol-2-yl)-2-fluorophenyl]methane sulfonamide (0.147 g).

HPLC purity 98.3% at 210-370 nm, 7.8 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{13}H_{12}FN_3O_2S+H^+$, 294.07070; found (ESI, $[M+H]^+$), 294.0696.

Example 12

N-[4-(5-cyano-1-methyl-1H-pyrrol-2-yl)-2-fluorophenyl]ethanesulfonamide 5-(4-amino-3-fluorophenyl)-1-methyl-1H-pyrrole-2-carbonitrile (0.31 g, 1.44 mmol) was dissolved in pyridine (3 mL), ethane sulfonyl chloride (0.12 mL, 1.3 mmol) was added, the mixture was stirred for 4 hours, and then water was added. The mixture diluted with ethyl acetate and the mixture was washed with water, saturated $CuSO_4$, 2N HCl, brine, dried over $MgSO_4$, and concentrated. Flash chromatography (5%-50% ethyl acetate in hexane) afforded N-[4-(5-cyano-1-methyl-1H-pyrrol-2-yl)-2-fluorophenyl]ethane sulfonamide (0.127 g). HPLC purity 100% at 210-370 nm, 8.3 min.; the Xterra™ RP18 instrument, 3.5/, 150×4.6 mm column, 1.2 mL/min., 85/15-5/95 (Ammon. Form. Buff. Ph=3.5/ACN+MeOH) for 10 min., hold 4 min. HRMS: calcd for $C_{14}H_{14}FN_3O_2S+H^+$, 308.08635; found (ESI, $[M+H]^+$), 308.0855.

Example 13

5-(4-amino-2-fluorophenyl)-1-methyl-1H-pyrrole-2-carbonitrile

4-Bromo-3-fluoroaniline (0.95 g, 5.0 mmol), 1-methyl-5-cyano-2-pyrroleboronic acid (1.35 g, 9.0 mmol), KF (0.96 g, 16.5 mmol), and $Pd_2(dba)_3$ (120 mg, 0.125 mmol) were added to a 50 mL round bottom flask under nitrogen. The flask was sealed and purged with nitrogen for 5 minutes. THF (12.5 mL) was added and the mixture was purged with nitrogen for an additional 5 minutes. A solution of tri-t-butylphosphine (10% wt in hexanes) (0.74 mL, 0.25 mmol) was added via syringe and the mixture was stirred vigorously at 25° C. for 16 hours. The mixture was diluted with 250 mL of EtOAc, filtered through a plug of silica gel, washed with 200 mL of EtOAc and concentrated to give a crude brown/black semi-solid. Purification via Isco chromatography (the Redisep® column, silica, gradient 5%-100% ethyl acetate in hexane) afforded 5-(4-amino-2-fluorophenyl)-1-methyl-1H-pyrrole-2-carbonitrile as a white solid (1.05 g, 98%).

HPLC purity 100.0% at 210-370 nm, 8.4 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 216.0.

Example 14

N-[4-(5-cyano-1-methyl-1H-pyrrol-2-yl)-3-fluorophenyl]methanesulfonamide 5-(4-amino-2-fluorophenyl)-1-methyl-1H-pyrrole-2-carbonitrile (0.20 g, 0.93 mmol) was dissolved in pyridine (2.0 mL). Methanesulfonyl chloride (0.07 mL, 0.9 mmol) was added and the mixture was stirred for 16 hours, followed by the addition of water. The mixture was diluted with ethyl acetate and then was washed with water, saturated $CuSO_4$, 2N HCl, brine, dried over $MgSO_4$, and concentrated. The crude product was purified via Isco chromatography (the Redisep® column, silica, gradient 5-50% ethyl acetate in hexane) to afford 0.18 g of N-[4-(5-cyano-1-methyl-1H-pyrrol-2-yl)-3-fluorophenyl]methanesulfonamide.

HPLC purity 100.0% at 210-370 nm, 8.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 293.9.

Example 15

N-[4-(5-cyano-1-methyl-1H-pyrrol-2-yl)-3-fluorophenyl]ethanesulfonamide

This compound was prepared according to the procedure described in Example 14 using ethane sulfonyl chloride (85 μL, 0.9 mmol) to provide N-[4-(5-cyano-1-methyl-1H-pyrrol-2-yl)-3-fluorophenyl]ethanesulfonamide (0.135 g).

HPLC purity 100.0% at 210-370 nm, 9.7 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. HRMS: calcd for $C_{14}H_{14}FN_3O_2S+H^+$, 308.08635; found (ESI, $[M+H]^+$), 308.0867.

Example 16

N-[4-(5-cyano-1-methyl-1H-pyrrol-2-yl)-3-fluorophenyl]propane-1-sulfonamide

The sulfonamide was prepared according to the procedure described in Example 14 using propane sulfonyl chloride (50 μL, 0.45 mmol) to provide N-[4-(5-cyano-1-methyl-1H-pyrrol-2-yl)-3-fluorophenyl]propane-1-sulfonamide (96 mg).

HPLC purity 99.2% at 210-370 nm, 9.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 321.9.

Example 17

N-[4-(5-cyano-1-methyl-1H-pyrrol-2-yl)-3-fluorophenyl]butane-1-sulfonamide

The sulfonamide was prepared according to the procedure described in Example 14 using butane sulfonyl chloride (58 μL, 0.45 mmol) to provide N-[4-(5-cyano-1-methyl-1H-pyrrol-2-yl)-3-fluorophenyl]butane-1-sulfonamide (60 mg).

HPLC purity 97.7% at 210-370 nm, 9.8 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 335.9.

Example 18

N-[4-(5-cyano-1-methyl-1H-pyrrol-2-yl)-3-fluorophenyl]propane-2-sulfonamide 5-(4-amino-2-fluorophenyl)-1-methyl-1H-pyrrole-2-carbonitrile (200 mg, 0.93 mmol) was dissolved in isopropyl sulfonyl chloride (0.50 mL, 2.8 mmol), pyridine (0.2 mL) was added and the mixture was heated to 100° C. for 6 hours. The mixture was then cooled and diluted with water and extracted with ethyl acetate. The organics were combined, washed with water, brine, dried over $MgSO_4$, and concentrated. Flash chromatography (0%-100% ethyl acetate in hexane) afforded N-[4-(5-cyano-1-methyl-1H-pyrrol-2-yl)-3-fluorophenyl]propane-2-sulfonamide (58 mg).

HPLC purity 92.5% at 210-370 nm, 9.2 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 321.9.

Example 19

5-(4-amino-2,5-difluorophenyl)-1-methyl-1H-pyrrole-2-carbonitrile

4-Bromo-2,5-difluoroaniline (0.1 g, 4.85 mmol), 1-methyl-5-cyano-2-pyrrole-boronic acid (1.3 g, 8.7 mmol), KF (0.93 g, 16 mmol), and $Pd_2(dba)_3$ (117 mg, 0.12 mmol) were added to a 50 mL round bottom flask under nitrogen. The flask was sealed and purged with nitrogen for 5 minutes. THF (12.1 mL) was added and the mixture was purged with nitrogen for an additional 5 minutes. A solution of tri-t-butylphosphine (10% wt in hexanes) (0.72 mL, 0.24 mmol) was added via syringe and the mixture was stirred vigorously at 25° C. for 16 hours. The mixture was diluted with 250 mL of EtOAc, filtered through a plug of silica gel, washed with 200 mL of EtOAc and concentrated to give a crude brown/black semi-solid. Purification via Isco chromatography (the Redisep® column, silica, gradient 5-100% ethyl acetate in hexane) afforded 5-(4-amino-2,5-difluorophenyl)-1-methyl-1H-pyrrole-2-carbonitrile as a white solid (0.87 g, 77%).

HPLC purity 100.0% at 210-370 nm, 8.9 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 234.0.

Example 20

N-[4-(5-cyano-1-methyl-1H-pyrrol-2-yl)-2,5-difluorophenyl]-methane-sulfonamide 5-(4-amino-2,5-difluorophenyl)-1-methyl-1H-pyrrole-2-carbonitrile (0.15 g, 0.64 mmol) was dissolved in pyridine (2.0 mL). Methanesulfonyl chloride (46 μL, 0.6 mmol) was added and the mixture was stirred for 16 hours, followed by the addition of water. The mixture was diluted with ethyl acetate, washed with water, saturated $CuSO_4$, 2N HCl, brine, dried over $MgSO_4$, and concentrated. The crude product was purified via Isco chromatography (the Redisep® column, silica, gradient 5-50% ethyl acetate in hexane) to afford 0.142 g of N-[4-(5-cyano-1-methyl-1H-pyrrol-2-yl)-2,5-difluorophenyl]-methane-sulfonamide.

HPLC purity 99.0% at 210-370 nm, 8.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 311.8.

Example 21

N-[4-(5-cyano-1-methyl-1H-pyrrol-2-yl)-2,5-difluorophenyl]ethane-sulfonamide

The sulfonamide was prepared according to procedure described in Example 20 using ethane sulfonyl chloride (56 μL, 0.6 mmol) to provide N-[4-(5-cyano-1-methyl-1H-pyrrol-2-yl)-2,5-difluorophenyl]ethane-sulfonamide (46 mg).

HPLC purity 100.0% at 210-370 nm, 8.7 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 323.9.

Example 22

N-[4-(5-cyano-1-methyl-1H-pyrrol-2-yl)-2,5-difluorophenyl]propane-1-sulfonamide

The sulfonamide was prepared according to the procedure described in Example 20 using propane sulfonyl chloride (67 μL, 0.6 mmol) to provide N-[4-(5-cyano-1-methyl-1H-pyrrol-2-yl)-2,5-difluorophenyl]propane-1-sulfonamide (41 mg).

HPLC purity 100.0% at 210-370 nm, 9.2 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 339.9.

Example 23

N-[4-(5-cyano-1-methyl-1H-pyrrol-2-yl)-2,5-difluorophenyl]butane-1-sulfonamide

The sulfonamide was prepared according to the procedure of Example 20 using butane sulfonyl chloride (77 μL, 0.6 mmol) to provide N-[4-(5-cyano-1-methyl-1H-pyrrol-2-yl)-2,5-difluorophenyl]butane-1-sulfonamide (28 mg).

HPLC purity 84.8% at 210-370 nm, 9.7 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 353.9.

Example 24

N-[4-(5-cyano-1-methyl-1H-pyrrol-2-yl)-2,5-difluorophenyl]propane-2-sulfonamide 5-(4-amino-2,5-difluorophenyl)-1-methyl-1H-pyrrole-2-carbonitrile (150 mg, 0.64 mmol) was dissolved in isopropyl sulfonyl chloride (1.0 mL, 9.0 mmol), pyridine (0.2 mL) was added and the mixture was heated to 100° C. for 6 hours. The mixture was then cooled, diluted with water and extracted with ethyl acetate. The organics were combined, washed with water, brine, dried over $MgSO_4$, and concentrated. Flash chromatography (0%-100% ethyl acetate in hexane) afforded N-[4-(5-cyano-1-methyl-1H-pyrrol-2-yl)-2,5-difluorophenyl]propane-2-sulfonamide (26 mg).

HPLC purity 97.6% at 210-370 nm, 9.1 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 339.9.

Example 25

5-[4-amino-2-(trifluoromethyl)phenyl]-1-methyl-1H-pyrrole-2-carbonitrile

4-Bromo-3-trifluoromethylaniline (1.77 g, 7.4 mmol), 1-methyl-5-cyano-2-pyrrole-boronic acid (2.0 g, 13.3 mmol), KF (1.42 g, 24.4 mmol), and $Pd_2(dba)_3$ (179 mg, 0.185 mmol) were added to a 50 mL round bottom flask under nitrogen. The flask was sealed and purged with nitrogen for 5 minutes. THF (18.5 mL) was added and the mixture was purged with nitrogen for an additional 5 minutes. A solution of tri-t-butylphosphine (10% wt in hexanes) (1.1 mL, 0.37 mmol) was added via syringe and the mixture was stirred vigorously at 25° C. for 16 hours. The mixture was diluted with 250 mL of EtOAc, filtered through a plug of silica gel, washed through with 200 mL of EtOAc and concentrated to give a crude brown/black semi-solid. Purification via Isco chromatography (the Redisep® column, silica, gradient 5-100% ethyl acetate in hexane) afforded 5-[4-amino-2-(trifluoromethyl)phenyl]-1-methyl-1H-pyrrole-2-carbonitrile as a white solid (1.8 g, 92%).

HPLC purity 100.0% at 210-370 nm, 9.1 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 266.1.

Example 26

N-[4-(5-cyano-1-methyl-1H-pyrrol-2-yl)-3-(trifluoromethyl)phenyl]methane-sulfonamide 5-[4-amino-2-(trifluoromethyl)phenyl]-1-methyl-1H-pyrrole-2-carbonitrile (0.34 g, 1.3 mmol) was dissolved in $CH_2Cl_2$ (5 mL) and pyridine (0.2 mL). Methanesulfonyl chloride (90 μL, 1.2 mmol) was added and the mixture was stirred for 16 hours followed by the addition of water. The mixture was then diluted with ethyl acetate, the mixture was washed with water, 2N HCl, brine, dried over $MgSO_4$, and concentrated. The crude product was purified via Isco chromatography (the Redisep® column, silica, gradient 5-50% ethyl acetate in hexane) to afford 0.29 g of N-[4-(5-cyano-1-methyl-1H-pyrrol-2-yl)-3-(trifluoromethyl)phenyl]-methanesulfonamide.

HPLC purity 98.2% at 210-370 nm, 9.0 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 341.8.

Example 27

N-[4-(5-cyano-1-methyl-1H-pyrrol-2-yl)-3-(trifluoromethyl)phenyl]ethane-sulfonamide The sulfonamide was prepared according to the procedure of Example 26 using ethane sulfonyl chloride (113 μL, 1.2 mmol) to provide N-[4-(5-cyano-1-methyl-1H-pyrrol-2-yl)-3-(trifluoromethyl)phenyl]ethane-sulfonamide (140 mg).

HPLC purity 100.0% at 210-370 nm, 9.3 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 355.8.

Example 28

N-[4-(5-cyano-1-methyl-1H-pyrrol-2-yl)-3-(trifluoromethyl)phenyl]propane-1-sulfonamide The sulfonamide was prepared according to the procedure of Example 26 using propyl sulfonyl chloride (134 μL, 1.2 mmol) to provide N-[4-(5-cyano-1-methyl-1H-pyrrol-2-yl)-3-(trifluoromethyl)phenyl]propane-1-sulfonamide (46 mg).

HPLC purity 99.6% at 210-370 nm, 9.7 min.; the Xterra™ RP18 instrument, 3.5μ, 150×4.6 mm column, 1.2 mL/min., 85/15-5/95 (Ammon. Form. Buff. Ph=3.5/ACN+MeOH) for 10 min., hold 4 min. MS (ES) m/z 371.8.

Example 29

N-[4-(5-cyano-1-methyl-1H-pyrrol-2-yl)-3-(trifluoromethyl)phenyl]butane-1-sulfonamide The sulfonamide was prepared according to the procedure of Example 26 using butyl sulfonyl chloride (163 µL, 1.2 mmol) to provide N-[4-(5-cyano-1-methyl-1H-pyrrol-2-yl)-3-(trifluoromethyl)phenyl]butane-1-sulfonamide (340 mg).

HPLC purity 99.0% at 210-370 nm, 10.1 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. MS (ES) m/z 385.9.

Example 30

N-[4-(5-cyano-1-methyl-1H-pyrrol-2-yl)-3-(trifluoromethyl)phenyl]propane-2-sulfonamide 5-[4-amino-2-(trifluoromethyl)phenyl]-1-methyl-1H-pyrrole-2-carbonitrile (0.33 g, 1.25 mmol) was dissolved in isopropyl sulfonyl chloride (1.0 mL, 9.0 mmol), pyridine (0.5 mL) was added, and the mixture was heated to 100° C. for 6 hours. The mixture was cooled and diluted with water and extracted with ethyl acetate. The organics were combined, washed with water, brine, dried over $MgSO_4$, and concentrated. Flash chromatography (0%-100% ethyl acetate in hexane) afforded N-[4-(5-cyano-1-methyl-1H-pyrrol-2-yl)-3-(trifluoromethyl)phenyl]-propane-2-sulfonamide (50 mg).

HPLC purity 95.4% at 210-370 nm, 9.6 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. MS (ES) m/z 371.9.

Example 31

5-[4-(1,1-dioxidoisothiazolidin-2-yl)phenyl)-1-methyl-1H-pyrrole-2-carbonitrile

Step 1:

4-Bromoaniline (0.86 g, 5.0 mmol) was dissolved in $CH_2Cl_2$ (15 mL), pyridine (0.5 mL) was added, and 3-chloropropanesulfonyl chloride (0.6 mL, 5.0 mmol) was added. The mixture was stirred for 4 hours, diluted with ethyl acetate, and then washed with water, 2N HCl, brine, dried over $MgSO_4$, and concentrated. The crude product was purified via Isco chromatography (the Redisep® column, silica, gradient 5-60% ethyl acetate in hexane) to afford 1.2 g (77%) N-(4-bromophenyl)-3-chloropropane-1-sulfonamide.

HPLC purity 98.4% at 210-370 nm, 9.3 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. MS (ES) m/z 311.6.

Step 2:

N-(4-Bromophenyl)-3-chloropropane-1-sulfonamide (1.0 g, 3.2 mmol) was dissolved in DMF, $Cs_2CO_3$ (1.56 g, 4.8 mmol) was added, and the mixture was stirred for 3 hours. The mixture was then diluted with ether, washed with water, 2N HCl, brine, dried over $MgSO_4$, and concentrated. The crude product was purified via Isco chromatography (the Redisep® column, silica, gradient 5-60% ethyl acetate in hexane) to afford 0.65 g (74%) 2-(4-bromophenyl)isothiazolidine 1,1-dioxide.

HPLC purity 100.0% at 210-370 nm, 7.9 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. MS (ES) m/z 275.7.

Step 3:

2-(4-Bromophenyl)isothiazolidine 1,1-dioxide (0.56 g, 2.0 mmol), 1-methyl-5-cyano-2-pyrroleboronic acid (0.36 g, 2.4 mmol), KF (0.38 g, 6.6 mmol), and $Pd_2(dba)_3$ (48 mg, 0.05 mmol) were added to a 50 mL round bottom flask under nitrogen. The flask was sealed and purged with nitrogen for 5 minutes. THF (5 mL) was added and the mixture was purged with nitrogen. A solution of tri-t-butylphosphine (10% wt in hexanes) (0.3 mL, 0.1 mmol) was added via syringe and the mixture was stirred vigorously at 25° C. for 16 hours. The mixture was diluted with EtOAc, filtered through a plug of silica gel, washed with 200 mL of EtOAc and concentrated to give a crude brown/black semi-solid. Purification via Isco chromatography (the Redisep® column, silica, gradient 5%-100% ethyl acetate in hexane) afforded 5-[4-(1,1-dioxidoisothiazolidin-2-yl)phenyl]-1-methyl-1H-pyrrole-2-carbonitrile as a white solid (54 mg).

HPLC purity 100.0% at 210-370 nm, 8.3 min.; the Xterra™ RP18 instrument, 3.5µ, 150×4.6 mm column, 1.2 mL/min., 85/15-5/95 (Ammon. Form. Buff. Ph=3.5/ACN+MeOH) for 10 min., hold 4 min. MS (ES) m/z 301.8.

Example 32

5-[4-amino-3-(trifluoromethoxy)phenyl]-1-methyl-1H-pyrrole-2-carbonitrile

4-Bromo-2-(trifluoromethoxy)aniline (1.3 g, 5.0 mmol), 5-cyano-1-methyl-1H-pyrrol-2-yl boronic acid (0.9 g, 6.0 mmol), potassium fluoride (0.96 g, 16.5 mmol), and tris(dibenzylideneacetone)dipalladium (0.12 g, 0.12 mmol) were placed in an oven dried flask under nitrogen and THF (12.5 mL) was added. Tri-t-butylphosphine (10 wt % in hexane) (0.356 mL, 0.24 mol) was added and the reaction was stirred for 16 hours. The reaction mixture was filtered through silica, rinsed with ethyl acetate, and concentrated. The crude product was pre-adsorbed onto the Celite™ reagent and purified via Isco chromatography (the Redisep® column, silica, gradient 5-30% ethyl acetate in hexane) to afford 1.0 g (71%) of 5-[4-amino-3-(trifluoromethoxy)phenyl]-1-methyl-1H-pyrrole-2-carbonitrile.

HPLC purity 98.2% at 210-370 nm, 9.6 min.; the Xterra™ RP18 instrument, 3.5µ, 150×4.6 mm column, 1.2 mL/min., 85/15-5/95 (Ammon. Form. Buff. PH=3.5/ACN+MeOH) for 10 min., hold 4 min. MS (ES) m/z 281.

Example 33

N-[4-(5-cyano-1-methyl-1H-pyrrol-2-yl)-2-(trifluoromethoxy)phenyl]methane-sulfonamide Methanesulfonyl chloride (0.05 mL, 0.65 mmol) was added dropwise to a solution of 5-[4-amino-3-(trifluoromethoxy)phenyl]-1-methyl-1H-pyrrole-2-carbonitrile (0.16 g, 0.56 mmol) in dry pyridine (2.0 mL). The solution was heated to 50° C. overnight. The solution was cooled to room temperature and pre-adsorbed onto the Celite™ reagent. The crude product was purified via Isco chromatography (the Redisep® column, silica, gradient 5-30% ethyl acetate in hexane) to afford 0.1 g (50%) of N-[4-(5-cyano-1-methyl-1H-pyrrol-2-yl)-2-(trifluoromethoxy)phenyl]methanesulfonamide.

HPLC purity 90.1% at 210-370 nm, 9.0 min.; the Xterra™ RP18 instrument, 3.5μ, 150×4.6 mm column, 1.2 mL/min., 85/15-5/95 (Ammon. Form. Buff. PH=3.5/ACN+MeOH) for 10 min., hold 4 min. MS (ES) m/z 359.

Example 34

N-[4-(5-cyano-1-methyl-1H-pyrrol-2-yl)-2-(trifluoromethoxy)phenyl]ethane-sulfonamide Using the procedure of Example 33, N-[4-(5-cyano-1-methyl-1H-pyrrol-2-yl)-2-(trifluoro-methoxy)phenyl] ethanesulfonamide was prepared using ethanesulfonyl chloride and 5-[4-amino-3-(trifluoromethoxy)phenyl]-1-methyl-1H-pyrrole-2-carbonitrile.

HPLC purity 92.5% at 210-370 nm, 9.4 min. the Xterra™ RP18 instrument, 3.5μ, 150×4.6 mm column, 1.2 mL/min., 85/15-5/95 (Ammon. Form. Buff. PH=3.5/ACN+MeOH) for 10 min., hold 4 min. MS (ES) m/z 373.

Example 35

N-[4-(5-cyano-1-methyl-1H-pyrrol-2-yl)-2-(trifluoromethoxy)phenyl]propane-1-sulfonamide Using the procedure of Example 33, N-[4-(5-cyano-1-methyl-1H-pyrrol-2-yl)-2-(trifluoro-methoxy)phenyl]propane-1-sulfonamide was prepared from propanesulfonyl chloride and 5-[4-amino-3-(trifluoromethoxy)phenyl]-1-methyl-1H-pyrrole-2-carbonitrile.

HPLC purity 94.5% at 210-370 nm, 9.8 min.; the Xterra™ RP18 instrument, 3.5μ, 150×4.6 mm column, 1.2 mL/min., 85/15-5/95 (Ammon. Form. Buff. PH=3.5/ACN+MeOH) for 10 min., hold 4 min. MS (ES) m/z 387.

Example 36

N-(4-bromophenyl)ethanesulfonamide

A mixture of ethanesulfonyl chloride (2.1 mL, 22 mmol), and 4-bromoaniline (3.44 g, 20 mmol) in pyridine (35 mL) was stirred at room temperature for 2 hours. The reaction mixture was acidified with 1N HCl solution and extracted with ether. The combined organic layers were dried over magnesium sulfate, and concentrated. The solid was triturated with hexane to afford the title compound (4.85 g, 92%).

HPLC purity component=100% at 210-370 nm; RT=8.2 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 37

Tert-butyl 2-{4-[(ethylsulfonyl)amino]phenyl}-1H-pyrrole-1-carboxylate

A mixture of N-(4-bromophenyl)ethanesulfonamide (1.88 g, 7.2 mmol), N-methylpyrrole-2-carbonitrile-5-boronic acid (2.11 g, 10 mmol), tetrakis(triphenylphosphine) palladium(0) (0.42 g, 0.36 mmol), and sodium carbonate (3.2 g, 30 mmol in 60 mL of water) in dimethoxyethane (200 mL) was heated to reflux for 4 hours. The mixture was cooled and partitioned between saturated ammonium chloride and ethyl acetate. The combined organic layers were dried over magnesium sulfate, and concentrated. The residue was purified by silica gel Flash Chromatography (hexane/ethyl acetate; 7:3) to afford the title compound (2.4 g, 97%).

HPLC purity component=95.8% at 210-370 nm; RT=9.8 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 38

Tert-butyl 2-cyano-5-{4-{(ethylsulfonyl)amino]phenyl}-1H-pyrrole-1-carboxylate tert-Butyl 2-{4-[(ethylsulfonyl)amino]phenyl}-1H-pyrrole-1-carboxylate (3.0 g, 8.58 mmol) was dissolved in tetrahydrofuran (85 mL) and cooled to −78° C., followed by the slow addition of chlorosulfonyl isocyanate. After tert-Butyl 2-{4-[(ethylsulfonyl)amino]phenyl}-1H-pyrrole-1-carboxylate was consumed, dimethyl formamide (6.86 mL) was added and the solution allowed to warm to room temperature. After 2 hours, the mixture was cooled and partitioned between water and diethyl ether. The combined organic layers were dried over magnesium sulfate, and concentrated. The residue was purified by silica gel flash chromatography (hexane/ethyl acetate; 7:3) to afford the title compound (1.84 g, 57%). The title compound was used immediately in the next step.

Example 39

N-[4-(5-cyano-1H-pyrrol-2-yl)phenyl]ethanesulfonamide

Tert-butyl-2-cyano-5-{4-{(ethylsulfonyl)amino]phenyl}-1H-pyrrole-1-carboxylate (2.3 g, 6.1 mmol) was dissolved in dimethylacetamide (60 mL) and heated to 170° C. for 30 minutes. The mixture was cooled and partitioned between water and ethyl acetate. The organic layers were dried over magnesium sulfate, and concentrated. The residue was purified by silica gel Flash Chromatography (hexane/ethyl acetate; 1:1) to afford the title compound (1.51 g, 90%).

HPLC purity component=100% at 210-370 nm; $R_T$=8.9 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{13}H_{13}N_3O_2S+H^+$, 275.3312; found (ESI-FTMS, $[M+H]^{1+}$), 276.075.

Example 40

N-[4-(5-cyano-1-ethyl-1H-pyrrol-2-yl)phenyl] ethanesulfonamide

N-[4-(5-cyano-1H-pyrrol-2-yl)phenyl]ethanesulfonamide (0.160 g, 0.58 mmol) was dissolved in tetrahydrofuran (10 mL). Potassium tert-butoxide (1.25 mL of a 1 M solution, 1.25 mmol) was dropwise added and the mixture stirred 15 minutes. Ethyl iodide (0.046 mL, 0.58 mmol) was dropwise added, followed by dimethyl formamide (5 mL) and the mixture stirred for 4 hours. The mixture was then partitioned between saturated ammonium chloride and ethyl acetate. The combined organic layers were dried over magnesium sulfate, and concentrated. The residue was purified by silica gel Flash Chromatography (hexane/ethyl acetate; 7:3) to afford the title compound (0.020 g, 11%).

HPLC purity component=100% at 210-370 nm; RT=8.9 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{15}H_{17}N_3O_2S+H^+$, 303.10415; found (ESI-FTMS, $[M+H]^{1+}$), 304.1109.

Example 41

N-[4-(5-cyano-1-propyl-1H-pyrrol-2-yl)phenyl]ethanesulfonamide

N-[4-(5-cyano-1H-pyrrol-2-yl)phenyl]ethanesulfonamide (0.150 g, 0.54 mmol) was alkylated according to the procedure of Example 40 using potassium tert-butoxide (1.08 mL of a 1 M solution, 1.08 mmol) and propyl iodide (0.056 mL, 0.50 mmol) to afford the title compound (0.10 g, 6.2%).

HPLC purity component=100% at 210-370 nm; RT=9.3 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{16}H_{19}N_3O_2S+H^+$, 317.1198; found (ESI-FTMS, $[M+H]^{1+}$), 318.1274.

Example 42

N-[4-(1-butyl-5-cyano-1H-pyrrol-2-yl)phenyl]ethanesulfonamide

N-[4-(5-cyano-1H-pyrrol-2-yl)phenyl]ethanesulfonamide (0.150 g, 0.54 mmol) was alkylated according to the procedure of Example 40 using potassium tert-butoxide (1.08 mL of a 1M solution, 1.08 mmol) and butyl iodide (0.066 mL, 0.50 mmol) to afford the title compound (0.10 g, 6%).

HPLC purity component=100% at 210-370 nm; RT=9.8 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{17}H_{21}N_3O_2S+H^+$, 331.1354; found (ESI-FTMS, $[M+H]^{1+}$), 332.1437.

Example 43

N-[4-(1-allyl-5-cyano-1H-pyrrol-2-yl)phenyl]ethanesulfonamide

N-[4-(5-cyano-1H-pyrrol-2-yl)phenyl]ethanesulfonamide (0.150 g, 0.54 mmol) was alkylated according to the procedure of Example 40 using potassium tert-butoxide (1.08 mL of a 1M solution, 1.08 mmol) and allyl bromide (0.041 mL, 0.50 mmol) to afford the title compound (0.10 g, 6.3%).

HPLC purity component=100% at 210-370 nm; $R_T$=9.0 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{16}H_{17}N_3O_2S+H^+$, 316.11142; found (ESI, $[M+H]^+$), 316.1126.

Example 44

N-[4-(5-cyano-1-prop-2-yn-1-yl-1H-pyrrol-2-yl)phenyl]ethanesulfonamide

N-[4-(5-cyano-1H-pyrrol-2-yl)phenyl]ethanesulfonamide (0.150 g, 0.54 mmol) was alkylated according to the procedure of Example 40 using potassium tert-butoxide (1.08 mL of a 1M solution, 1.08 mmol) and propargyl bromide (80% in toluene, 0.055 mL, 0.50 mmol) to afford the title compound (0.10 g, 6.3%).

HPLC purity component=99% at 210-370 nm; RT=8.5 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{16}H_{15}N_3O_2S+H^+$, 313.0885; found (ESI-FTMS, $[M+H]^{1+}$), 314.0971.

Example 45

N-{4-[5-cyano-1-(3-phenylpropyl)-1H-pyrrol-2-yl]phenyl}ethanesulfonamide

N-[4-(5-cyano-1H-pyrrol-2-yl)phenyl]ethanesulfonamide (0.150 g, 0.54 mmol) was alkylated according to the procedure of Example 40 using potassium tert-butoxide (1.08 mL of a 1 M solution, 1.08 mmol) and 1-Iodo-3-phenylpropane (0.093 mL, 0.60 mmol) to afford the title compound (0.020 g, 10%).

HPLC purity component=100% at 210-370 nm; RT=10.4 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{22}H_{23}N_3O_2S+H^+$, 393.1511; found (ESI-FTMS, $[M+H]^{1+}$), 394.1566.

Example 46

5-amino-2-chlorobenzonitrile

A mixture of 2-chloro-5-nitrobenzonitrile (10 g, 54.8 mmol) and stannous chloride dihydrate (56 g, 248.6 mmol) in isopropyl alcohol (125 mL) and concentrated hydrochloric acid solution (62.5 mL) was heated to reflux for 1 hour. The mixture was then cooled and neutralized with sodium hydroxide solution (2N). The aqueous layer was extracted with methylene chloride. The combined organic layers were dried over magnesium sulfate and concentrated to afford the title compound (8 g, 96%).

HPLC purity component=100% at 210-370 nm; RT=7.2 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 47

5-(4-amino-2-cyanophenyl)-1-methyl-1H-pyrrole-2-carbonitrile

A mixture of 5-amino-2-chlorobenzonitrile (1.3 g, 8.58 mmol), tris(dibenzylideneacetone)dipalladium (0.192 g, 0.209 mmol), N-methyl-5-cyanopyrroleboronic acid (2.55 g, 17.16 mmol), and potassium fluoride (1.81 g, 31.25 mmol) in tetrahydrofuran (20 mL) was stirred under nitrogen. Tri-tert-butylphosphine (10% solution in hexane, 1.23 mL, 0.414 mmol) was added to the mixture and allowed to stir 3 hours at 50° C. until the starting bromide was consumed. The mixture was then diluted with 1/1 hexane/tetrahydrofuran and filtered through a plug of silica gel. The solvent was evaporated and the residue was purified by silica gel column chromatography (hexane/ethylacetate, 90/10 to 50/50) to afford the title compound (1.77 g, 92%).

HPLC purity component=98% at 210-370 nm; RT=7.8 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 48

N-[3-cyano-4-(5-cyano-1-methyl-1H-pyrrol-2-yl)phenyl]methanesulfonamide

A mixture of methanesulfonyl chloride (0.074 mL, 1 mmol) and 5-(4-amino-2-cyanophenyl)-1-methyl-1H-pyrrole-2-carbonitrile (0.166 g, 0.75 mmol) in pyridine (1 mL) was heated to 50° C. for 4 hours. The reaction mixture was acidified with 1N HCl solution and extracted with ethyl acetate. The combined organic layers were dried over magnesium sulfate and concentrated. The residue was purified by silica gel column chromatography (hexane/ethylacetate, 90/10 to 60/40) to afford the title compound (0.059 g, 33%).

HPLC purity component=98.1% at 210-370 nm; RT=9.1 min.; 85/15-5/95 (Ammon. Form. Buff. Ph=3.5/ACN+MeOH) for 10 min., hold 4 min. the Xterra™ RP18 instrument, 3.5μ, 150×4.6 mm, 1.2 mL/min. HRMS: calcd for $C_{14}H_{12}N_4O_2S+H^+$, 300.341; found (ESI-FTMS, $[M+H]^{1+}$), 301.0744.

Example 49

N-[3-cyano-4-(5-cyano-1-methyl-1H-pyrrol-2-yl)phenyl]ethanesulfonamide

This compound was prepared according to the procedure of Example 48 using ethanesulfonyl chloride (0.094 mL, 1 mmol) to afford the title compound (0.079 g, 42%).

HPLC purity component=95.9% at 210-370 nm; RT=9.6 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{15}H_{14}N_4O_2S+H^+$, 314.3679; found (ESI-FTMS, $[M+H]^{1+}$), 315.0908.

Example 50

N-[3-cyano-4-(5-cyano-1-methyl-1H-pyrrol-2-yl)phenyl]propane-1-sulfonamide

This compound was prepared according to the procedure described in Example 48 using propanesulfonyl chloride (0.115 mL, 1 mmol) to afford the title compound (0.100 g, 50%). HPLC purity component=96.6% at 210-370 nm; RT=10.3 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{16}H_{16}N_4O_2S+H^+$, 328.3948; found (ESI-FTMS, $[M+H]^{1+}$), 329.1069.

Example 51

N-[2-cyano-4-(5-cyano-1-methyl-1H-pyrrol-2-yl)phenyl]methanesulfonamide

This compound was prepared according to the procedure of Example 48 using methane-sulfonyl chloride (0.044 mL, 0.6 mmol) and 5-(4-amino-3-cyanophenyl)-1-methyl-1H-pyrrole-2-carbonitrile (0.100 g, 0.45 mmol) to afford the title compound (0.100 g, 50%).

HPLC purity component=96.6% at 210-370 nm; RT=10.3 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{14}H_{12}N_4O_2S+H^+$, 300.0681; found (ESI-FTMS, $[M+H]^{1+}$), 301.10763.

Example 52

5-(4-amino-2,6-difluorophenyl)-1-methyl-1H-pyrrole-2-carbonitrile

A mixture of 4-bromo-3,5-difluoroaniline (0.782 g, 3.78 mmol), tris(dibenzylidene-acetone)dipalladium (0.096 g, 0.105 mmol), N-methyl-5-cyanopyrroleboronic acid (1.12 g, 7.46 mmol), and potassium fluoride (0.789 g, 13.6 mmol) in THF (10 mL) was stirred under nitrogen. Tri-tert-butylphosphine (10% solution in hexane, 0.621 mL, 0.210 mmol) was added to the mixture and allowed to stir until the starting bromide was consumed. The mixture was then diluted with 1/1 hexane/tetrahydrofuran, filtered through a plug of silica gel, the solvent evaporated and the residue purified by silica gel column chromatography (hexane/ethylacetate, 70/30) to afford the title compound (1.77 g, 92%).

HPLC purity component=100% at 210-370 mm; RT=8.8 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min. HRMS: calcd for $C_{12}H_9F_2N_3+H^+$, 233.0764; found (ESI-FTMS, $[M+H]^{1+}$), 234.0433.

Example 53

N-[4-(5-cyano-1-methyl-1H-pyrrol-2-yl)-3,5-difluorophenyl]-methanesulfonamide

A mixture of methanesulfonyl chloride (0.046 mL, 0.66 mmol) and 5-(4-amino-2,6-difluorophenyl)-1-methyl-1H-pyrrole-2-carbonitrile (0.100 g, 0.429 mmol) in pyridine (1.5 mL) was heated to 50° C. for 4 hours. The reaction mixture was acidified with 1N HCl solution and extracted with ethyl acetate. The combined organic layers were dried over magnesium sulfate, and concentrated. The residue was purified by silica gel column chromatography (dichloromethane/acetone, 97/3) to afford the title compound (0.060 g, 45%).

HPLC purity component=100% at 210-370 nm; RT=8.7 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 54

N-[4-(5-cyano-1-methyl-1H-pyrrol-2-yl)-3,5-difluorophenyl]ethane-sulfonamide

This compound was prepared according to the procedure of Example 53 using ethanesulfonyl chloride (0.062 mL, 0.66 mmol). The residue was purified by silica gel column chromatography (dichloromethane/acetone, 98/2) to afford the title compound (0.050 g, 35%).

HPLC purity component=100% at 210-370 nm; RT=9.1 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 55

N-[4-(5-cyano-1-methyl-1H-pyrrol-2-yl)-3,5-difluorophenyl]propane-1-sulfonamide

This compound was prepared according to the procedure of Example 53 using propanesulfonyl chloride (0.076 mL, 0.66 mmol). The residue was purified by silica gel column chromatography (dichloromethane/acetone, 99/1) to afford the title compound (0.025 g, 17%).

HPLC purity component=99.4% at 210-370 nm; RT=9.6 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 56

N-[4-(5-cyano-1-methyl-1H-pyrrol-2-yl)-3,5-difluorophenyl]butane-1-sulfonamide

This compound was prepared according to the procedure of Example 53 using butanesulfonyl chloride (0.084 mL, 0.66 mmol). The residue was purified by silica gel column chromatography (dichloromethane/acetone, 99/1) to afford the title compound (0.025 g, 16%).

HPLC purity component=100% at 210-370 nm; RT=10 min.; 85/15-5/95 (Ammon. Form. Buff. Ph=3.5/ACN+MeOH) for 10 min., hold 4 min the Xterra™ RP18 instrument, 3.5μ, 150×4.6 mm, 1.2 mL/min.

Example 57

Pharmacology

An assay was performed to identify compounds having progesterone receptor modulator activity. This assay identifies progestins or antiprogestins by determining a compound's effect on alkaline phosphatase activity in T47D cells.

A. Reagents:

Culture medium: DMEM:F12 (1:1) (GIBCO, BRL) supplemented with 5% (v/v) charcoal stripped fetal bovine serum (not heat-inactivated), 100 U/mL penicillin, 100 μg/mL streptomycin, and 2 mM the GlutaMax™ reagent (GIBCO, BRL).

Alkaline phosphatase assay buffer:

I. 0.1M Tris-HCl, pH 9.8, containing 0.2% the Triton™ X-100 reagent

II. 0.1M Tris-HCl, pH 9.8, containing 4 mM p-nitrophenyl phosphate (Sigma).

B. Cell Culture and Treatment:

Frozen T47D cells are thawed in a 37° C. water bath and diluted to 280,000 cells/mL in culture medium. To each well in a 96-well plate (Falcon, Becton Dickinson Labware), 180 μL of diluted cell suspension is added.

Twenty 1 μL of reference or test compounds diluted in the culture medium is then added to each well. When testing for progestin antagonist activity, reference antiprogestins or test compounds are added in the presence of 1 nM progesterone. The cells are incubated at 37° C. in a 5% $CO_2$/humidified atmosphere for 24 hours.

For high throughput screening, one concentration of each compound will be tested at 0.3 μg/mL. Based on an average molecular weight of 300 g/mol for the compounds in the library, the concentration is approximately 1 μM. Subsequently, active compounds will be tested in dose response assays to determine $EC_{50}$ and $IC_{50}$.

C. Alkaline Phosphatase Enzyme Assay:

At the end of treatment, the medium is removed from the plate. Fifty μL of assay buffer I is added to each well. The plates are shaken in a titer plate shaker for 15 min. Then 150 μL of assay buffer II is added to each well. Optical density measurements are taken at 5 minute intervals for 30 minutes at a test wavelength of 405 nM.

D. Analysis of Results:

Analysis of dose-response data. For reference and test compounds, a dose response curve is generated for dose (x-axis) vs. the rate of enzyme reaction (slope) (y-axis). Square root-transformed data are used for analysis of variance and nonlinear dose response curve fitting for both agonist and antagonist modes. Huber weighting is used to down-weight the effects of outliers. $EC_{50}$ or $IC_{50}$ values are calculated from the retransformed values. JMP software (SAS Institute, Inc.) is used for both one-way analysis of variance and nonlinear dose response analysis in both single dose and dose response studies.

E. Reference Compounds:

Progesterone and trimegestone are reference progestins and RU486 is the reference antiprogestin. All reference compounds are run in full dose response curves and the $EC_{50}$ and $IC_{50}$ values are calculated.

| Example # | Compound Name | $IC_{50}$ (nM) | Active Dose (nM) | Inhibition (%) |
|---|---|---|---|---|
| 1 | N-[4-(5-cyano-1-methyl-1H-pyrrol-2-yl)phenyl]propane-1-sulfonamide | 9.8 | | |
| 2 | N-[4-(5-cyano-1-methyl-1H-pyrrol-2-yl)phenyl]-N-(methylsulfonyl)methanesulfonamide | ~300 | | |
| 3 | N-[4-(5-cyano-1-methyl-1H-pyrrol-2-yl)phenyl]butane-1-sulfonamide | ~300 | | |
| 4 | N-[4-(5-cyano-1-methyl-1H-pyrrol-2-yl)phenyl]-2,2,2-trifluoroethanesulfonamide | 58.4 | | |
| 5 | N-[4-(5-cyano-1-methyl-1H-pyrrol-2-yl)phenyl]-4-isopropylbenzenesulfonamide | ~3000 | | |
| 6 | N-[4-(5-cyano-1-methyl-1H-pyrrol-2-yl)phenyl]benzenesulfonamide | ~30 | | |
| 7 | N-[4-(5-cyano-1-methyl-1H-pyrrol-2-yl)phenyl]-4-methylbenzenesulfonamide | ~3000 | | |
| 8 | N-[4-(5-cyano-1-methyl-1H-pyrrol-2-yl)phenyl]propane-2-sulfonamide | 1.5 | | |
| 9 | N-[4-(5-cyano-1-methyl-1H-pyrrol-2-yl)phenyl]ethanesulfonamide | 10 | | |
| 10 | N-[4-(5-cyano-1-methyl-1H-pyrrol-2-yl)phenyl]methanesulfonamide | 8.2 | | |

-continued

| Example # | Compound Name | $IC_{50}$ (nM) | Active Dose (nM) | Inhibition (%) |
|---|---|---|---|---|
| 11 | N-[4-(5-cyano-1-methyl-1H-pyrrol-2-yl)-2-fluorophenyl]methanesulfonamide | 28.9 | | |
| 12 | N-[4-(5-cyano-1-methyl-1H-pyrrol-2-yl)-2-fluorophenyl]ethanesulfonamide | 29.9 | | |
| 14 | N-[4-(5-cyano-1-methyl-1H-pyrrol-2-yl)-3-fluorophenyl]methanesulfonamide | 18.3 | 10000 | |
| 15 | N-[4-(5-cyano-1-methyl-1H-pyrrol-2-yl)-3-fluorophenyl]ethanesulfonamide | 3.8 | 10000 | |
| 16 | N-[4-(5-cyano-1-methyl-1H-pyrrol-2-yl)-3-fluorophenyl]propane-1-sulfonamide | 3.5 | | |
| 17 | N-[4-(5-cyano-1-methyl-1H-pyrrol-2-yl)-3-fluorophenyl]butane-1-sulfonamide | 6.6 | | |
| 18 | N-[4-(5-cyano-1-methyl-1H-pyrrol-2-yl)-3-fluorophenyl]propane-2-sulfonamide | 9.3 | 10000 | |
| 20 | N-[4-(5-cyano-1-methyl-1H-pyrrol-2-yl)-2,5-difluorophenyl]-methane-sulfonamide | 39.8 | 10000 | |
| 21 | N-[4-(5-cyano-1-methyl-1H-pyrrol-2-yl)-2,5-difluorophenyl]ethane-sulfonamide | 22.1 | | |
| 23 | N-[4-(5-cyano-1-methyl-1H-pyrrol-2-yl)-2,5-difluorophenyl]butane-1-sulfonamide | 266.6 | | |
| 24 | N-[4-(5-cyano-1-methyl-1H-pyrrol-2-yl)-2,5-difluorophenyl]propane-2-sulfonamide | 230.8 | | |
| 26 | N-[4-(5-cyano-1-methyl-1H-pyrrol-2-yl)-3-(trifluoromethyl)phenyl]methanesulfonamide | 13.4 | | |
| 27 | N-[4-(5-cyano-1-methyl-1H-pyrrol-2-yl)-3-(trifluoromethyl)phenyl]ethane-sulfonamide | 10.2 | | |
| 28 | N-[4-(5-cyano-1-methyl-1H-pyrrol-2-yl)-3-(trifluoromethyl)phenyl]propane-1-sulfonamide | 9.4 | | |
| 29 | N-[4-(5-cyano-1-methyl-1H-pyrrol-2-yl)-3-(trifluoromethyl)phenyl]butane-1-sulfonamide | 53.7 | | |
| 30 | N-[4-(5-cyano-1-methyl-1H-pyrrol-2-yl)-3-(trifluoromethyl)phenyl]propane-2-sulfonamide | 25.2 | | |
| 31 | 5-[4-(1,1-dioxidoisothiazolidin-2-yl)phenyl]-1-methyl-1H-pyrrole-2-carbonitrile | 179.5 | | |
| 33 | N-[4-(5-cyano-1-methyl-1H-pyrrol-2-yl)-2-(trifluoromethoxy)phenyl]methane-sulfonamide | 32.2 | | |
| 34 | N-[4-(5-cyano-1-methyl-1H-pyrrol-2-yl)-2-(trifluoromethoxy)phenyl]ethane-sulfonamide | 35.8 | | |
| 35 | N-[4-(5-cyano-1-methyl-1H-pyrrol-2-yl)-2-(trifluoromethoxy)phenyl]propane-1-sulfonamide | 40.7 | | |
| 39 | N-[4-(5-cyano-1H-pyrrol-2-yl)phenyl]ethanesulfonamide | 68.6 | | |
| 40 | N-[4-(5-cyano-1-ethyl-1H-pyrrol-2-yl)phenyl]ethanesulfonamide | 84.1 | | |
| 41 | N-[4-(5-cyano-1-propyl-1H-pyrrol-2-yl)phenyl]ethanesulfonamide | 721.4 | | |
| 42 | N-[4-(1-butyl-5-cyano-1H-pyrrol-2-yl)phenyl]ethanesulfonamide | 545.6 | | |
| 43 | N-[4-(1-allyl-5-cyano-1H-pyrrol-2-yl)phenyl]ethanesulfonamide | 600.1 | | |
| 44 | N-[4-(5-cyano-1-prop-2-yn-1-yl-1H-pyrrol-2-yl)phenyl]ethanesulfonamide | 796.5 | | |
| 45 | N-{4-[5-cyano-1-(3-phenylpropyl)-1H-pyrrol-2-yl]phenyl}ethanesulfonamide | | 3000 | 15 |
| 48 | N-[3-cyano-4-(5-cyano-1-methyl-1H-pyrrol-2-yl)phenyl]methanesulfonamide | 198.4 | | |
| 49 | N-[3-cyano-4-(5-cyano-1-methyl-1H-pyrrol-2-yl)phenyl]ethanesulfonamide | 123.8 | | |
| 50 | N-[3-cyano-4-(5-cyano-1-methyl-1H-pyrrol-2-yl)phenyl]propane-1-sulfonamide | 86.8 | | |
| 51 | N-[2-cyano-4-(5-cyano-1-methyl-1H-pyrrol-2-yl)phenyl]methanesulfonamide | | 3000 | 50 |
| 53 | N-[4-(5-cyano-1-methyl-1H-pyrrol-2-yl)-3,5-difluorophenyl]-methanesulfonamide | 16 | | |
| 54 | N-[4-(5-cyano-1-methyl-1H-pyrrol-2-yl)-3,5-difluorophenyl]ethane-sulfonamide | 19 | | |
| 55 | N-[4-(5-cyano-1-methyl-1H-pyrrol-2-yl)-3,5-difluorophenyl]propane-1-sulfonamide | 6.2 | | |
| 56 | N-[4-(5-cyano-1-methyl-1H-pyrrol-2-yl)-3,5-difluorophenyl]butane-1-sulfonamide | 8.6 | | |

In the table provided above, the $IC_{50}$ values show the relative progesterone receptor antagonist activity in this assay. Lower numbers are indicative of higher potency, i.e., greater PR antagonist activity. The assay has a standard deviation of about ±6. Further, compounds 45 and 51 gave 15 and 50% inhibition, respectively, at an active dose of 3000 nM.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A compound having the structure of formula I, or a pharmaceutically acceptable salt thereof:

I

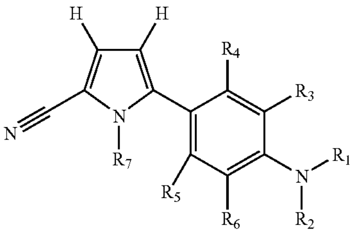

wherein:

$R_1$ is selected from the group consisting of:

H,

CN, $SO_2$—$C_1$-$C_6$ alkyl, $SO_2$—$C_3$-$C_8$ cycloalkyl, $SO_2$-substituted $C_1$-$C_6$ alkyl, $SO_2$-aryl, $SO_2$-substituted aryl, $SO_2$-heteroaryl, $SO_2$-heterocycle, $SO_2$—$C_3$-$C_6$ alkenyl, $SO_2$—$C_3$-$C_6$ alkynyl, $SO_2$—$C_3$-$C_6$ substituted alkenyl, $SO_2$—$C_3$-$C_6$ substituted alkynyl, C(O)—$C_1$-$C_6$ alkyl, C(O)—$C_3$-$C_8$ cycloalkyl, C(O)-substituted $C_1$-$C_6$ alkyl, C(O)-aryl, C(O)-substituted aryl, C(O)-heteroaryl, C(O)-heterocycle, C(O)—$C_3$-$C_6$ alkenyl, C(O)—$C_3$-$C_6$ alkynyl, C(O)-substituted $C_3$-$C_6$ alkenyl, C(O)-substituted $C_3$-$C_6$ alkynyl, C(O)O—$C_1$-$C_6$ alkyl, C(O)O—$C_3$-$C_8$ cycloalkyl, C(O)O-substituted $C_1$-$C_6$ alkyl, C(O)O-aryl, C(O)O-substituted aryl, C(O)O-heteroaryl, C(O)O-heterocycle, C(O)O—$C_3$-$C_6$ alkenyl, C(O)O—$C_3$-$C_6$ alkynyl, C(O)O—$C_3$-$C_6$ substituted alkenyl, C(O)O—$C_3$-$C_6$ substituted alkynyl, C(O)NH—$C_1$-$C_6$ alkyl, C(O)NH—$C_3$-$C_8$ cycloalkyl, C(O)N-di-$C_3$-$C_8$ cycloalkyl, C(O)N-di-$C_1$-$C_6$ alkyl, C(O)N-di-substituted $C_1$-$C_6$ alkyl, C(O)NH-substituted $C_1$-$C_6$ alkyl, C(O)NH-aryl, C(O)N-di-aryl, C(O)NH-substituted aryl, C(O)N-diaryl, C(O)NH-heteroaryl, C(O)NH-heterocycle, C(O)N-diheteroaryl, C(O)N-diheterocycle, C(O)NH—$C_3$-$C_6$ alkenyl, C(O)NH—$C_3$-$C_6$ alkynyl, C(O)NH-substituted $C_3$-$C_6$ alkenyl, and C(O)NH-substituted $C_3$-$C_6$ alkynyl; or $R_1$ is a linking group to a second structure of formula I to form a dimer of formula I, said linking group selected from the group consisting of C(O)— and $S(O)_2$—;

$R_2$ is selected from the group consisting of H, $C_1$-$C_6$ alkyl, substituted $C_1$-$C_6$ alkyl, $C_3$-$C_6$ cycloalkyl, $SO_2$-alkyl, and $SO_2$-substituted alkyl;

provided that at least one of $R_1$ or $R_2$ contain a group having an $SO_2$— bound to the N or $R_1$ is a $S(O)_2$— linking group; or $R_1$ and $R_2$ are joined to form —$(C(R_8)_a(R_9)_b)_c$—$SO_2$—$(C(R_5)_d(R_9)_e)_f$—;

$R_8$ and $R_9$ are, independently, H, halogen, or $C_1$ to $C_6$ alkyl;

a and b are, independently, 0 to 2, provided that a+b=2;

d and e are, independently, 0 to 2, provided that a+b=2;

c and f are, independently, 0 to 5, provided that one of c or f is greater than 0;

$R_3$, $R_4$, $R_5$ and $R_6$ are independently selected from the group consisting of H, halogen, CN, $C_1$-$C_6$ alkyl, substituted $C_1$-$C_6$ alkyl, —$(CH_mX_n)_zCH_pX_q$, $C_3$-$C_6$ cycloalkyl, O—$C_1$-$C_6$ alkyl, O—$C_1$-$C_6$ substituted alkyl, O—$(CH_mX_n)_zCH_pX_q$, aryl, heteroaryl, heterocycle, substituted aryl, substituted heteroaryl, substituted heterocycle;

X is halogen;

m and n are, independently, 0 to 2, provided that m+n=2;

p and q are, independently, 0 to 3, provided that p+q=3; and z is 0 to 10;

$R_7$ is selected from the group consisting of H, $C_1$-$C_6$ alkyl, C(O)O—$C_1$-$C_6$ alkyl, $C_2$ to $C_6$ alkenyl, $C_2$ to $C_6$ alkynyl, substituted $C_1$-$C_6$ alkyl, $C_3$-$C_6$ cycloalkyl, and substituted $C_3$-$C_6$ cycloalkyl.

2. The compound according to claim 1, wherein:

$R_1$ is selected from the group consisting of $SO_2$—$C_1$-$C_6$ alkyl, $SO_2$—$C_3$-$C_8$ cycloalkyl, $SO_2$-substituted $C_1$-$C_6$ alkyl, $SO_2$-aryl, $SO_2$-substituted aryl, $SO_2$-heteroaryl, CN, $SO_2$—$C_3$-$C_6$ alkenyl, $SO_2$—$C_3$-$C_6$ alkynyl, $SO_2$—$C_3$-$C_6$ substituted alkenyl, and $SO_2$—$C_3$-$C_6$ substituted alkynyl;

$R_2$ is H or $C_1$-$C_6$ alkyl;

$R_3$, $R_4$, $R_5$ and $R_6$ are independently selected from the group consisting of H, halogen, $C_1$-$C_6$ alkyl, $C_3$-$C_6$ cycloalkyl, O—$C_1$-$C_6$ alkyl, and O—$C_1$-$C_6$ substituted alkyl; and $R_7$ is H or $C_1$-$C_6$ alkyl.

3. The compound according to claim 1, wherein:

$R_1$ is selected from the group consisting of $SO_2$—$C_1$-$C_4$ alkyl, $SO_2$—$C_3$-$C_5$ cycloalkyl, and CN;

$R_2$ is H;

$R_3$, $R_4$, $R_5$ and $R_6$ are independently selected from the group consisting of H, halogen, $C_1$-$C_6$ alkyl, O—$C_1$-$C_6$ alkyl, —$(CH_mX_n)_zCH_pX_q$, and O—$(CH_mX_n)_zCH_pX_q$; and $R_7$ is H or $C_1$-$C_6$ alkyl.

4. The compound according to claim 1, wherein:

$R_1$ is $SO_2$—$C_1$-$C_4$ alkyl;

$R_2$ is H;

each of $R_3$, $R_4$, $R_5$ and $R_6$ is H or F; and $R_7$ is $C_1$-$C_6$ alkyl.

5. The compound according to claim 1, wherein:

$R_1$ is $SO_2$—$C_3$-$C_5$ cycloalkyl;

$R_2$ is H;

$R_3$, $R_4$, $R_5$ and $R_6$ are, independently, H or F; and $R_7$ is $C_1$ alkyl.

6. The compound according to claim 1, wherein:

$R_1$ is $SO_2$—$C_3$-$C_6$ alkyl;

$R_2$ is H;

$R_3$, $R_4$, $R_5$ and $R_6$ are, independently, H or F; and $R_7$ is $C_1$ alkyl.

7. The compound according to claim 1, wherein:

$R_1$ is selected from the group consisting of $SO_2$-substituted $C_2$-$C_6$ alkyl, wherein the alkyl is substituted with one or more halogen, and $CF_3$.

8. The compound according to claim 1, wherein:

$R_1$ is a C(O) linking group to a second structure of formula (I) to form a dimer thereof.

9. The compound according to claim 1, wherein:

$R_2$ is selected from the group consisting of H and $SO_2$—$C_1$-$C_4$ alkyl.

10. The compound according to claim 1, wherein:

$R_3$ is selected from the group consisting of H, $C_1$-$C_3$ alkyl, a halogen selected from the group consisting of F and Cl, and O—$C_1$-$C_3$ alkyl.

11. The compound according to claim 1, wherein:

$R_4$ is selected from the group consisting of H and O—$C_1$-$C_3$ alkyl.

12. The compound according to claim 1, wherein:

$R_5$ is selected from the group consisting of H, $C_1$-$C_3$ alkyl, a halogen selected from the group consisting of F and Cl, and O—$C_1$-$C_3$ alkyl.

13. The compound according to claim 1, wherein:

$R_6$ is selected from the group consisting of H and halogen, wherein the halogen is F.

14. The compound according to claim 1, wherein:

$R_7$ is $C_1$ alkyl.

15. The compound according to claim 1, wherein the compound is selected from the group consisting of:

N-[4-(5-cyano-1-methyl-1H-pyrrol-2-yl)phenyl]propane-1-sulfonamide;

N-[4-(5-cyano-1-methyl-1H-pyrrol-2-yl)phenyl]-N-(methylsulfonyl)methane sulfonamide;

N-[4-(5-cyano-1-methyl-1H-pyrrol-2-yl)phenyl]butane-1-sulfonamide;

N-[4-(5-cyano-1-methyl-1H-pyrrol-2-yl)phenyl]-2,2,2-trifluoroethanesulfonamide;

N-[4-(5-cyano-1-methyl-1H-pyrrol-2-yl)phenyl]-4-isopropylbenzenesulfonamide;

N-[4-(5-cyano-1-methyl-1H-pyrrol-2-yl)phenyl]benzenesulfonamide;

N-[4-(5-cyano-1-methyl-1H-pyrrol-2-yl)phenyl]-4-methylbenzenesulfonamide;

N-[4-(5-cyano-1-methyl-1H-pyrrol-2-yl)phenyl]propane-2-sulfonamide;

N-[4-(5-cyano-1-methyl-1H-pyrrol-2-yl)phenyl]ethanesulfonamide;

N-[4-(5-cyano-1-methyl-1H-pyrrol-2-yl)phenyl]methanesulfonamide

N-[4-(5-cyano-1-methyl-1H-pyrrol-2-yl)-2-fluorophenyl]methanesulfonamide;

N-[4-(5-cyano-1-methyl-1H-pyrrol-2-yl)-2-fluorophenyl]ethanesulfonamide;

N-[4-(5-cyano-1-methyl-1H-pyrrol-2-yl)-3-fluorophenyl]ethanesulfonamide;

N-[4-(5-cyano-1-methyl-1H-pyrrol-2-yl)-3-fluorophenyl]propane-1-sulfonamide;

N-[4-(5-cyano-1-methyl-1H-pyrrol-2-yl)-3-fluorophenyl]butane-1-sulfonamide;

N-[4-(5-cyano-1-methyl-1H-pyrrol-2-yl)-3-fluorophenyl]propane-2-sulfonamide;

N-[4-(5-cyano-1-methyl-1H-pyrrol-2-yl)-2,5-difluorophenyl]-methane-sulfonamide;

N-[4-(5-cyano-1-methyl-1H-pyrrol-2-yl)-2,5-difluorophenyl]ethane-sulfonamide;

N-[4-(5-cyano-1-methyl-1H-pyrrol-2-yl)-2,5-difluorophenyl]propane-1-sulfonamide;

N-[4-(5-cyano-1-methyl-1H-pyrrol-2-yl)-2,5-difluorophenyl]butane-1-sulfonamide;

N-[4-(5-cyano-1-methyl-1H-pyrrol-2-yl)-2,5-difluorophenyl]propane-2-sulfonamide;

N-[4-(5-cyano-1-methyl-1H-pyrrol-2-yl)-3-(trifluoromethyl)phenyl]methane-sulfonamide;

N-[4-(5-cyano-1-methyl-1H-pyrrol-2-yl)-3-(trifluoromethyl)phenyl]ethane-sulfonamide;

N-[4-(5-cyano-1-methyl-1H-pyrrol-2-yl)-3-(trifluoromethyl)phenyl]propane-1-sulfonamide;

N-[4-(5-cyano-1-methyl-1H-pyrrol-2-yl)-3-(trifluoromethyl)phenyl]butane-1-sulfonamide;

N-[4-(5-cyano-1-methyl-1H-pyrrol-2-yl)-3-(trifluoromethyl)phenyl]propane-2-sulfonamide;

N-[4-(5-cyano-1-methyl-1H-pyrrol-2-yl)-2-(trifluoromethoxy)phenyl]methane-sulfonamide;

N-[4-(5-cyano-1-methyl-1H-pyrrol-2-yl)-2-(trifluoromethoxy)phenyl]ethane-sulfonamide;

N-[4-(5-cyano-1-methyl-1H-pyrrol-2-yl)-2-(trifluoromethoxy)phenyl]propane-1-sulfonamide;

N-(4-bromophenyl)ethanesulfonamide;

Tert-butyl 2-cyano-5-{4-{(ethylsulfonyl)amino]phenyl}-1H-pyrrole-1-carboxylate;

N-[4-(5-cyano-1H-pyrrol-2-yl)phenyl]ethanesulfonamide;

N-[4-(5-cyano-1-ethyl-1H-pyrrol-2-yl)phenyl]ethanesulfonamide;

N-[4-(5-cyano-1-propyl-1H-pyrrol-2-yl)phenyl]ethanesulfonamide;

N-[4-(1-butyl-5-cyano-1H-pyrrol-2-yl)phenyl]ethanesulfonamide;

N-[4-(1-allyl-5-cyano-1H-pyrrol-2-yl)phenyl]ethanesulfonamide;

N-[4-(5-cyano-1-prop-2-yn-1-yl-1H-pyrrol-2-yl)phenyl]ethanesulfonamide;

N-{4-[5-cyano-1-(3-phenylpropyl)-1H-pyrrol-2-yl]phenyl}ethanesulfonamide;

N-[3-cyano-4-(5-cyano-1-methyl-1H-pyrrol-2-yl)phenyl]methanesulfonamide;

N-[3-cyano-4-(5-cyano-1-methyl-1H-pyrrol-2-yl)phenyl]ethanesulfonamide;

N-[3-cyano-4-(5-cyano-1-methyl-1H-pyrrol-2-yl)phenyl]propane-1-sulfonamide;

N-[2-cyano-4-(5-cyano-1-methyl-1H-pyrrol-2-yl)phenyl]methanesulfonamide;

N-[4-(5-cyano-1-methyl-1H-pyrrol-2-yl)-3,5-difluorophenyl]-methanesulfonamide;

N-[4-(5-cyano-1-methyl-1H-pyrrol-2-yl)-3,5-difluorophenyl]ethane-sulfonamide;

N-[4-(5-cyano-1-methyl-1H-pyrrol-2-yl)-3,5-difluorophenyl]propane-1-sulfonamide;

N-[4-(5-cyano-1-methyl-1H-pyrrol-2-yl)-3,5-difluorophenyl]butane-1-sulfonamide; and N-[4-(5-cyano-1-methyl-1H-pyrrol-2-yl)-3-fluorophenyl]methanesulfonamide.

16. A pharmaceutical composition comprising a compound according to claim 1 and a pharmaceutically acceptable carrier.

17. The pharmaceutical composition according to claim 16, wherein said composition is an oral dosage unit.

18. The pharmaceutical composition according to claim 16, wherein said composition is a solid oral dosage unit.

19. The pharmaceutical composition according to claim 16, wherein said composition further comprises an estrogen.

20. The pharmaceutical composition according to claim 16, wherein said composition further comprises a progestin.

* * * * *

UNITED STATES PATENT AND TRADEMARK OFFICE

CERTIFICATE OF CORRECTION

PATENT NO. : 7,291,643 B2
APPLICATION NO. : 11/494226
DATED : November 6, 2007
INVENTOR(S) : McComas et al.

It is certified that error appears in the above-identified patent and that said Letters Patent is hereby corrected as shown below:

Col. 38, line 2, replace "(C($R_5$)" with -- (C($R_8$) --.

Signed and Sealed this

Twentieth Day of May, 2008

JON W. DUDAS

*Director of the United States Patent and Trademark Office*